United States Patent [19]

Davis et al.

[11] Patent Number: 5,258,289
[45] Date of Patent: Nov. 2, 1993

[54] METHOD FOR THE SELECTING OF GENES ENCODING CATALYTIC ANTIBODIES

[76] Inventors: Claude G. Davis, 10 Mercato Ct., San Francisco, Calif. 94131; Gary R. Fabian, 1163 Ruby St., Redwood City, Calif. 94061

[21] Appl. No.: 780,765

[22] Filed: Oct. 22, 1991

Related U.S. Application Data

[63] Continuation-in-part of Ser. No. 577,906, Sep. 5, 1990, abandoned.

[51] Int. Cl.⁵ .................... C12N 15/00; C12N 15/13
[52] U.S. Cl. ................... 435/69.6; 435/69.7; 435/172.3; 424/85.8
[58] Field of Search .................. 424/85.8; 435/69.6, 435/172.3, 69.7

[56] References Cited

U.S. PATENT DOCUMENTS

| | | | |
|---|---|---|---|
| 4,336,186 | 6/1982 | Garguilo et al. | 260/112.5 |
| 4,895,719 | 1/1990 | Radhakrishnan et al. | 424/45 |
| 5,037,750 | 8/1991 | Schochetman et al. | 435/183 |

OTHER PUBLICATIONS

Cross, C. E., "Pathogenic Mechanisms in Asthma" in *Bronchial Asthma*, Second Edition, Grunc & Stratton, 1986.
Goldman, K., et al., FEBS Letters 190(2):319-323 (1985).
Helm, B., et al., Nature 331:180-183 (1988).
Helm, B., et al., Proc. Natl. Acad. Sci. USA 86:9465-9469 (1989).
Huse, W. D., et al., Science 246:1275-1281 (1989).
Morrison, S. L., et al., Proc. Natl. Acad. Sci. USA 81:6851-6855 (1984).
Yamada, M., et al., Proc. Natl. Acad. Sci. USA 79:2827-2831 (1982).

*Primary Examiner*—Robert J. Hill, Jr.
*Assistant Examiner*—John D. Ulm
*Attorney, Agent, or Firm*—Gary R. Fabian; Peter J. Dehlinger

[57] ABSTRACT

The present invention describes methods of screening for or selecting a catalytic antibody effective to cleave a target peptide. In particular, in the selection method of the present invention a phage gene is selected that encodes a gene product necessary for the production of a phage. The phage, carrying the modified gene is introduced into a host. Also, a library of rearranged immunoglobulin genes in a cloning vector is introduced into host cells. The host cells are grown under conditions in which the immunoglobulin genes are expressed in the host cells. The presence of antibodies capable of cleaving the target peptide is identified on the basis of production of phage.

8 Claims, 18 Drawing Sheets

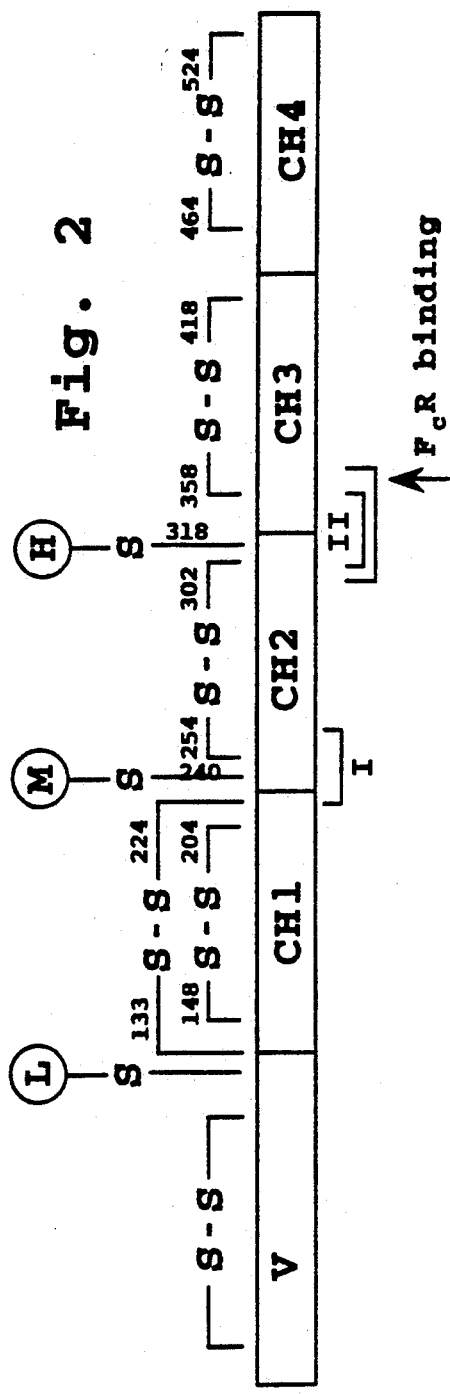

Fig. 2

120 ASTQSPSVFP LTRCCKNIPS NATSVTLGCL ATGYFPEPVM VTWDTGSLNG TTMTLPATTL TLSGHYATIS

190 LLTVSGAWAK QMFTCRVAHT PSSTDWVDNK TFSVCSRDFT PPTVKILQSS CDGGGHFPPT IQLLCLVSGY

260 TPGTINITWL EDGQVMDVDL STASTTQEGE LASTQSELTL SQKHWLSDRT YTCQVTYQGH TFEDSTKKCA

330 DSNPRGVSAT LSRPSPPDLF IRKSPTITCL VVDLAPSKGT VNLTWSRASG KPVNHSTRKE EKQRNGTLTV
                                                         FcR binding domain

400 TSTLPVGTRD WIEGETYQCR VTHPHLPRAL MRSTTKTSGP RAAPEVYAFA TPEWPGSRDK RTLACLIENF

470 MPEDISVQWL HNEVQLPDAR HSTTQPRKTK GSGFFVFSRL EVTRAEWEQK DEFICRAVHE AASPSQTVQR

540 AVSVNPGK

Fig. 3

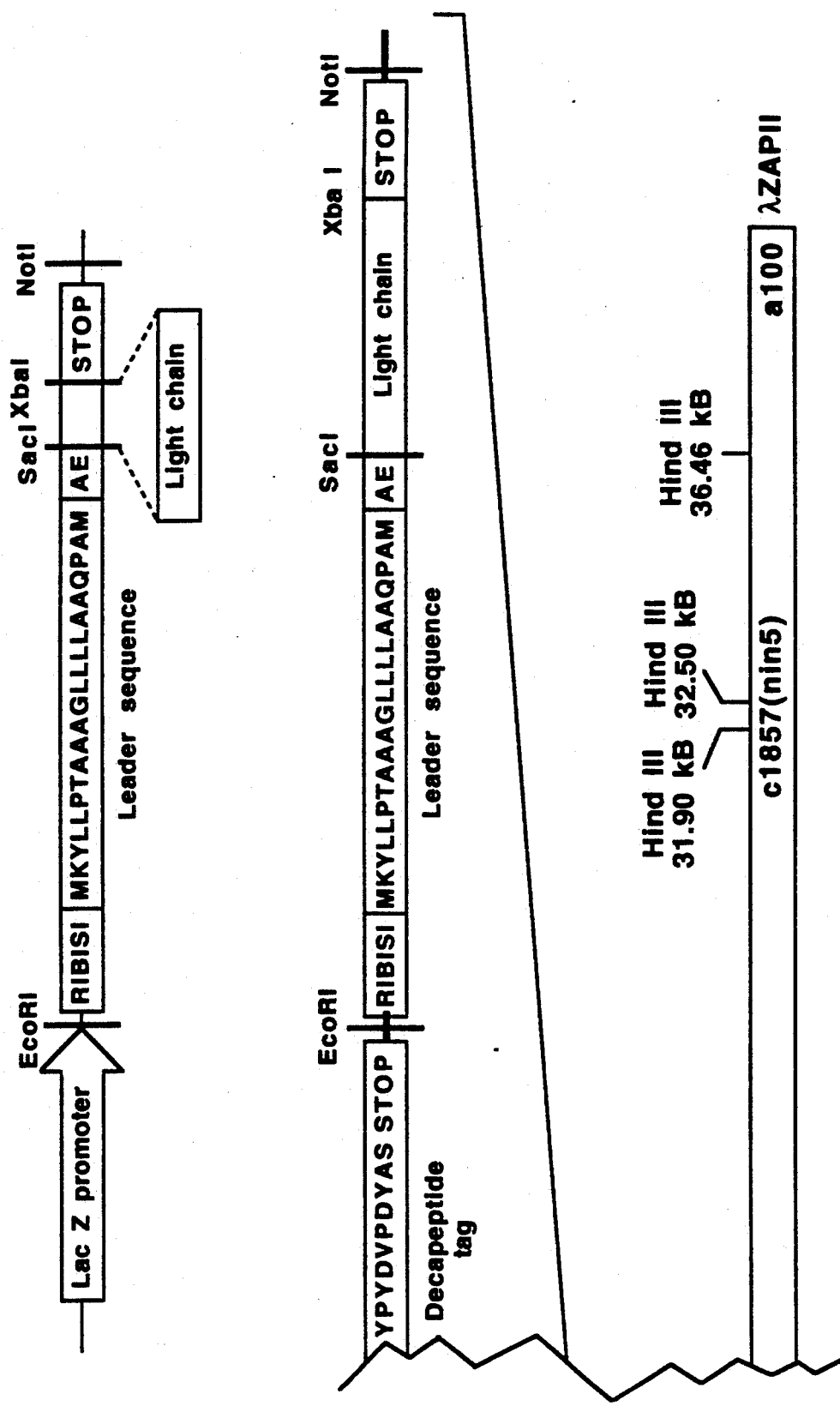
Fig. 4 (con't)

O = TARGET PEPTIDE

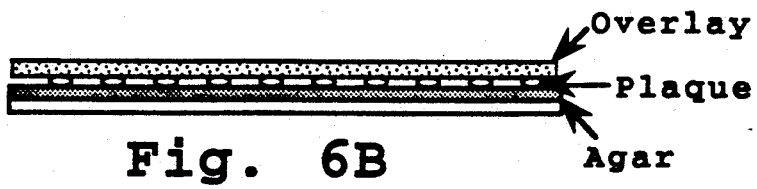
Fig. 6B
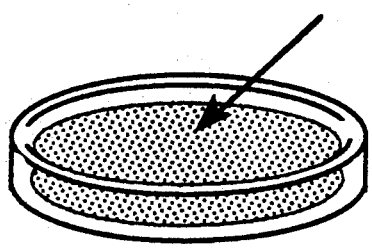
Fig. 6A
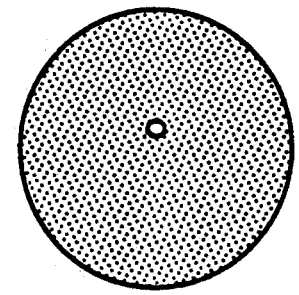
Fig. 6C
Fig. 8A
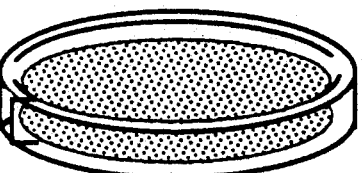
Fig. 8B
Fig. 8C
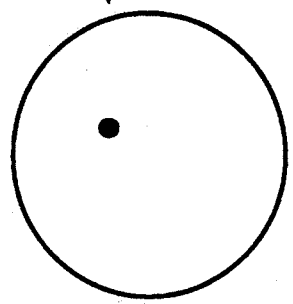
Fig. 8D Protected-amino peptide Fluorescence assay for free amino groups

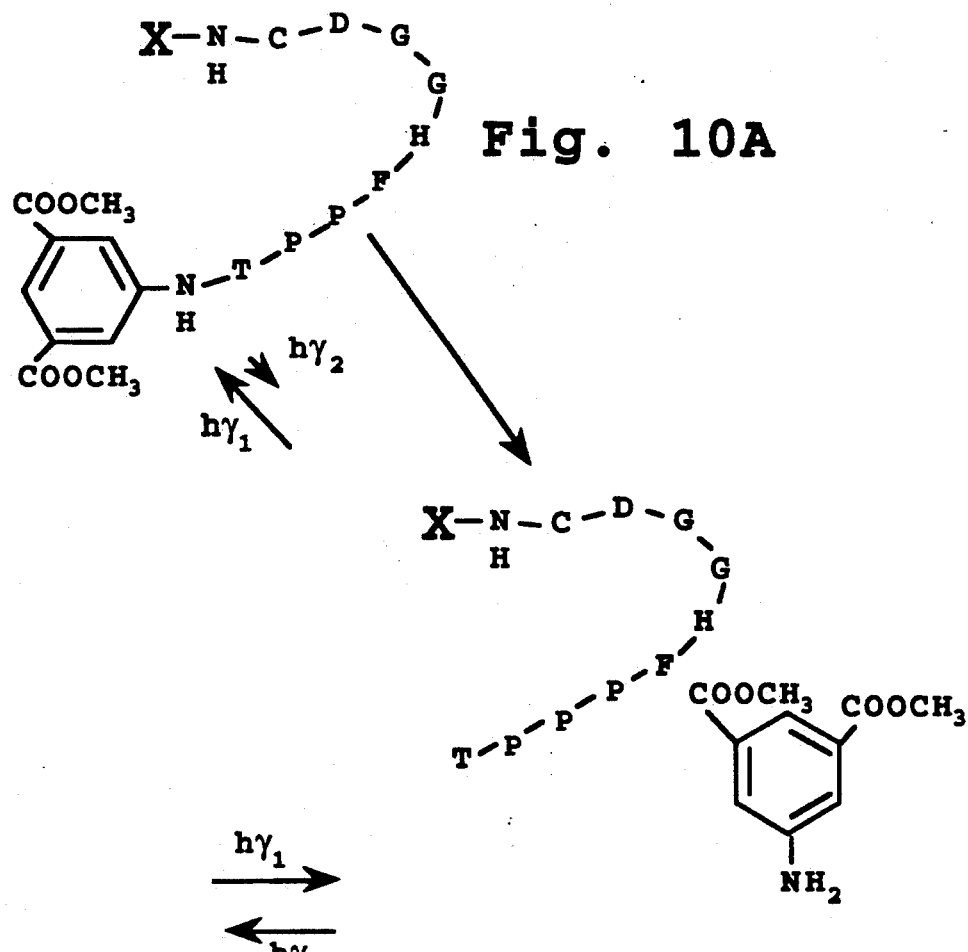
Fig. 10A
Fig. 10B
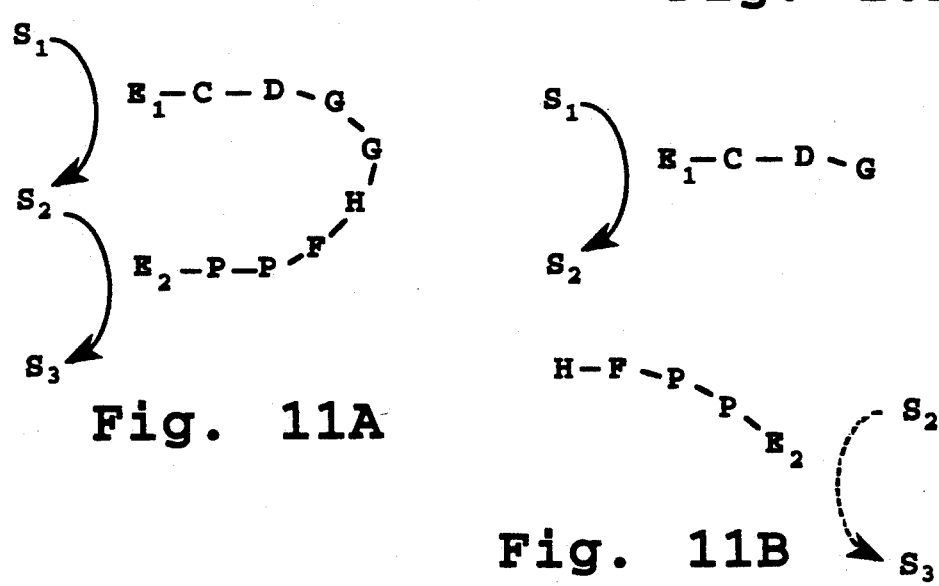
Fig. 11A
Fig. 11B

Infect and plate

↓ 42°C

↓ Select viable plaque-generating phage

METHOD FOR THE SELECTING OF GENES ENCODING CATALYTIC ANTIBODIES

This application is a continuation-in-part of co-pending, co-owned U.S. application Ser. No. 07/577,906, filed 5 Sep. 1990, abandoned.

1. FIELD OF THE INVENTION

The present invention relates to screening and selection methods effective for the identification of catalytic antibodies capable of cleaving a specified peptide sequence. In particular, the selection of antibodies capable of cleaving IgE molecules.

2. REFERENCES

Arber, W., et al., in *Lambda II*, edited by R. W. Hendrix et al., Cold Spring Harbor Laboratory, Cold Spring Harbor N.Y., pages 433–466 (1983).
Ausubel, F. M., et al., *Current Protocols in Molecular Biology*, John Wiley and Sons, Inc., Media Pa.
Better, M., et al., Science 240:1041 (1988).
Ciccarelli, E., et al., Biochem. Biophys. Res. Commun. 161:865 (1989).
Crea, R., U.S. Pat. No. 4,888,286, issued Dec. 19, 1989.
Cross, C. E., in *Bronchial Asthma: Principles of Diagnosis and Treatment*, Second Edition, M. E. Gershwin, Ed., Publ. Grune and Stratton (Harcourt Brace Jovanovich), pages 39–47 (1986).
Davis, R. W., et al., *A manual for genetic engineering. Advanced Bacterial Genetics*, Cold Spring Harbor Laboratory, Cold Spring Harbor N.Y. (1980).
Dayhoff, M. O., et al., Methods in Enzymology 91:524 (1983).
Dooittle, R. F., Science 214:149 (1981).
Eaton, M. A. W., et al., U.S. Pat. No. 4,719,180, issued Jan. 12, 1988.
Gargiulo, R. J., et al., U.S. Pat. No 4,336,186, issued Jun. 22, 1982.
Goldman, K., et al., FEBS Letters 190(2):319 (1985).
Gussin, G. N., et al., in *Lambda II*, edited by R. W. Hendrix, et al., Cold Spring Harbor Laboratory, Cold Spring Harbor N.Y., pages 93–121 (1983).
Helm, B., et al., Nature 331:180 (1988).
Helm, B., et al., Proc. Natl. Acad. Sci. 86:9465 (1989).
Hubacek, J., et al., J. Mol. Biol. 50:111 (1970).
Huse, W. D., et al., Science 246:1275 (1989).
Hussain, K., et al., Mol. Microbiol. 1(1):73 (1987).
Ishizaka, T., et al., Immunochemistry 7:687 (1970).
Jones, E. W., Genetics 85:23, (1977).
Jones, E. W., et al., *Alfred Benzon Symposium*, ed. D. von Wettstein, et al., 16:183, Copenhagen, Munksgaard.
Kabat, E. A., et al., *Sequences of Proteins of Immunological Interest*, U. S. Public Health Service, National Institutes of Health, Bethesda, Md. (1987).
Maniatis, T., et al., *Molecular Cloning: A Laboratory Manual*, Cold Spring Harbor Laboratories, Cold Spring Harbor, N.Y. (1982).
Miller, J. H., *Experiments in molecular genetics.*, Cold Spring Harbor Laboratories, Cold Spring Harbor, N.Y. (1972).
Mieschendahl, M., et al., J. Bacteriol. 164(3):1366 (1985).
Morrison, S., et al., Proc. Natl. Acad. Sci. 81:6851 (1984).
Mullis, K., U.S. Pat. No. 4,683,202, issued Jul. 28, 1987.
Needleman, S. B., et al., J. Mol. Biol. 48:443 (1970).
Oka, A., et al., Mol. Gen. Genet. 172:151 (1982).
O'Shannessy, D. J., et al., Immun. Letters 8:273 (1984).
Ovchinnikov, Y. A., et al., Gene 6:235 (1979).
Radhakrishnan, R., et al., U.S. Pat. No. 4,895,719, issued Jan. 23, 1990.
Roberts, T. M., et al., Nature 270:274 (1977).
Short, J. M., et al., Nucleic Acids Res. 16:7583 (1988).
Skerra, A., et al., Science 240:1038 (1988).
Smith, R. E., U.S. Pat. No. 3,862,011.
Sutcliffe, J. G., et al., Cold Spring Harbor Symp. Quant. Biol. 43:77 (1978).
Ullmann, A., Gene 29:27 (1984).
Weisberg, R. A., et al., Virology 95:99 (1979).
Woo, S. L. C., Methods in Enzymology 68:389 (1979).
Yoshio, T., et al., U.S. Pat. No. 4,849,350, issued Jul. 18, 1989.
Yamada, M., et al., Proc. Natl. Acad. Sci. U.S.A. 79:2827 (1982).

3. BACKGROUND OF THE INVENTION

When a foreign substance is introduced into the human body, the individual typically reacts by mounting an immune response by generating antibodies to this substance. A second encounter with the same substance usually elicits a faster and stronger response. In most cases, this response gives protection from the clinical course of an infection (immunity). However, the immune response is not always beneficial, as in the case where the substance provokes an antibody-mediated allergic response. About 5 to 10% of the world population suffer from allergies, and it has been estimated that 30–35 million U.S. citizens (15% of the population) suffer from at least one significant allergy.

The central molecule of the most common allergies is the antibody of the immunoglobulin E class (IgE). In terms of mass, IgE constitutes only a minute segment of total serum. Serum immunoglobulin levels of IgE are in the range of 200 nanograms (ng) per milliliter (ml), as compared to 12 mg/ml for IgG and 1 mg/ml for IgM. The low levels of IgE raises the question of its physiological function. There is evidence that IgE may play a role in the body's defense against large parasites like worms, but, if so, it is only marginally effective. Generally parasitic infections require treatment with anti-parasite drugs, and, in any case, parasites are generally not considered to be a health problem outside of third-world countries. There is no other known beneficial role of IgE.

The first step in an allergic reaction is the binding of an allergen to IgE molecules which are anchored to the surface of mast cells and basophils via specific receptors (IgE/Fc receptors). Attempts to block IgE/Fc receptors with isolated Fc fragments have been reported (Helm et al., 1989). This approach has two limitations. First, the affinity of the Fc fragment for the Fc receptor is about tenfold lower than that of an intact IgE molecule, making it necessary to administer high concentrations in order to effectively block IgE binding. Secondly, injection of this fragment at high concentrations may result in an immune response to the fragment itself. If antibodies to Fc were indeed generated, they would crosslink Fc fragments on the Fc receptors and thereby activate every mast cell and basophil. This could result in anaphylactic shock.

A second approach currently being tested is to administer antibodies which bind the Fc receptor-binding domain of the IgE molecule. These antibodies essentially absorb IgE from the circulation and prevent it from binding to mast cells and basophils. The shortcomings of this approach are (1) that the antibodies will not effectively bind IgE molecules already bound to Fc receptors, and (2) the antibodies must be administered in high doses, thus increasing the risks of complications.

4. SUMMARY OF THE INVENTION

The present invention describes a method of selecting a catalytic antibody effective to cleave a target peptide. In this method a target peptide is chosen. Also, a phage gene is selected that encodes a gene product necessary for the production of a phage. This gene is modified by introducing the target peptide coding sequence into the gene such that the resulting gene product:

(i) inhibits production of infectious phage, and
(ii) cleavage of said target peptide results in an active gene product that allows production of infectious phage.

The phage, carrying the modified gene is introduced into a host. Also, a library of rearranged immunoglobulin genes in a cloning vector is introduced into host cells: this vector library is capable of expressing immunoglobulin genes in the cloning vector, under suitable expression conditions. The host cells are grown under conditions in which the immunoglobulin genes are expressed in the host cells. The presence of antibodies capable of cleaving the target peptide is identified on the basis of production of phage.

5. BRIEF DESCRIPTION OF THE DRAWINGS

FIG. 2 shows a schematic of an IgE molecule including the various domains, disulphide linkages, and carbohydrate groups and indicates the location of peptides I and II as well as the region which binds the IgE Fc receptor;

FIG. 3 gives the amino acid sequence of the constant region of an IgE heavy chain; peptides I and II as well as the FcR binding domain are underlined.

Figure 4:
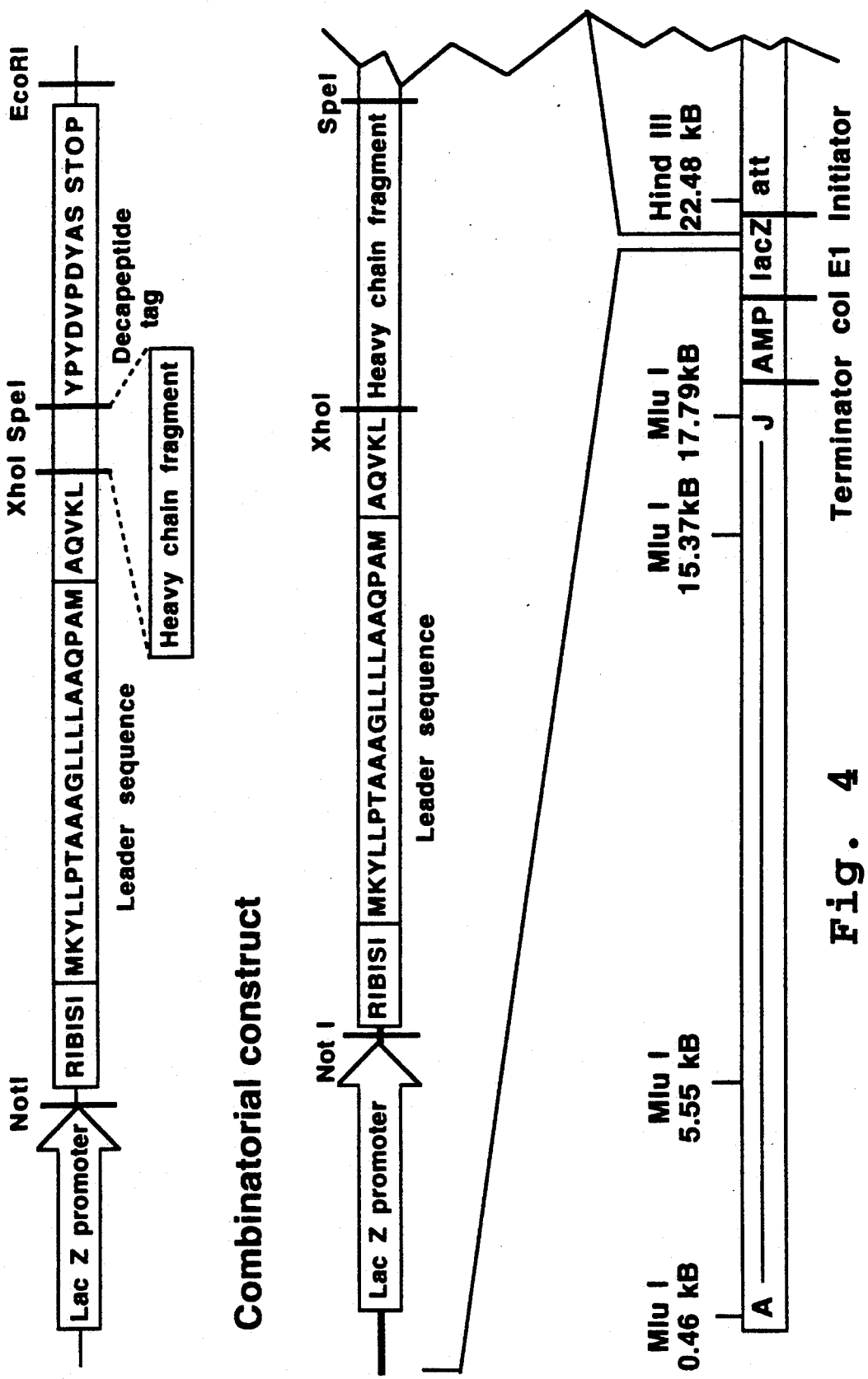
Figure 5C:
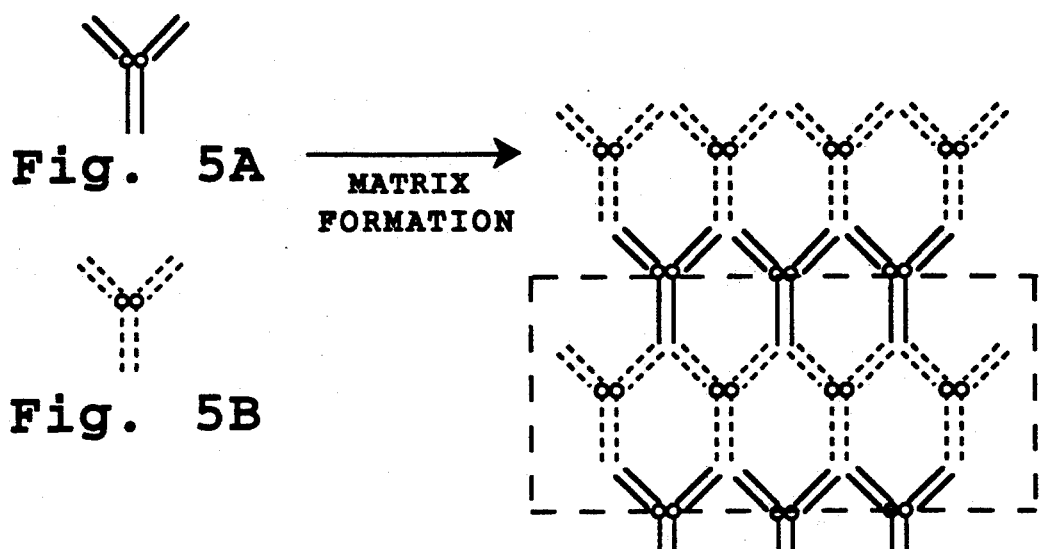
Figure 5D:
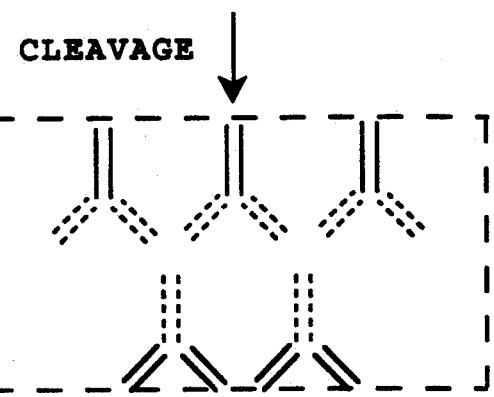
Figure 12:
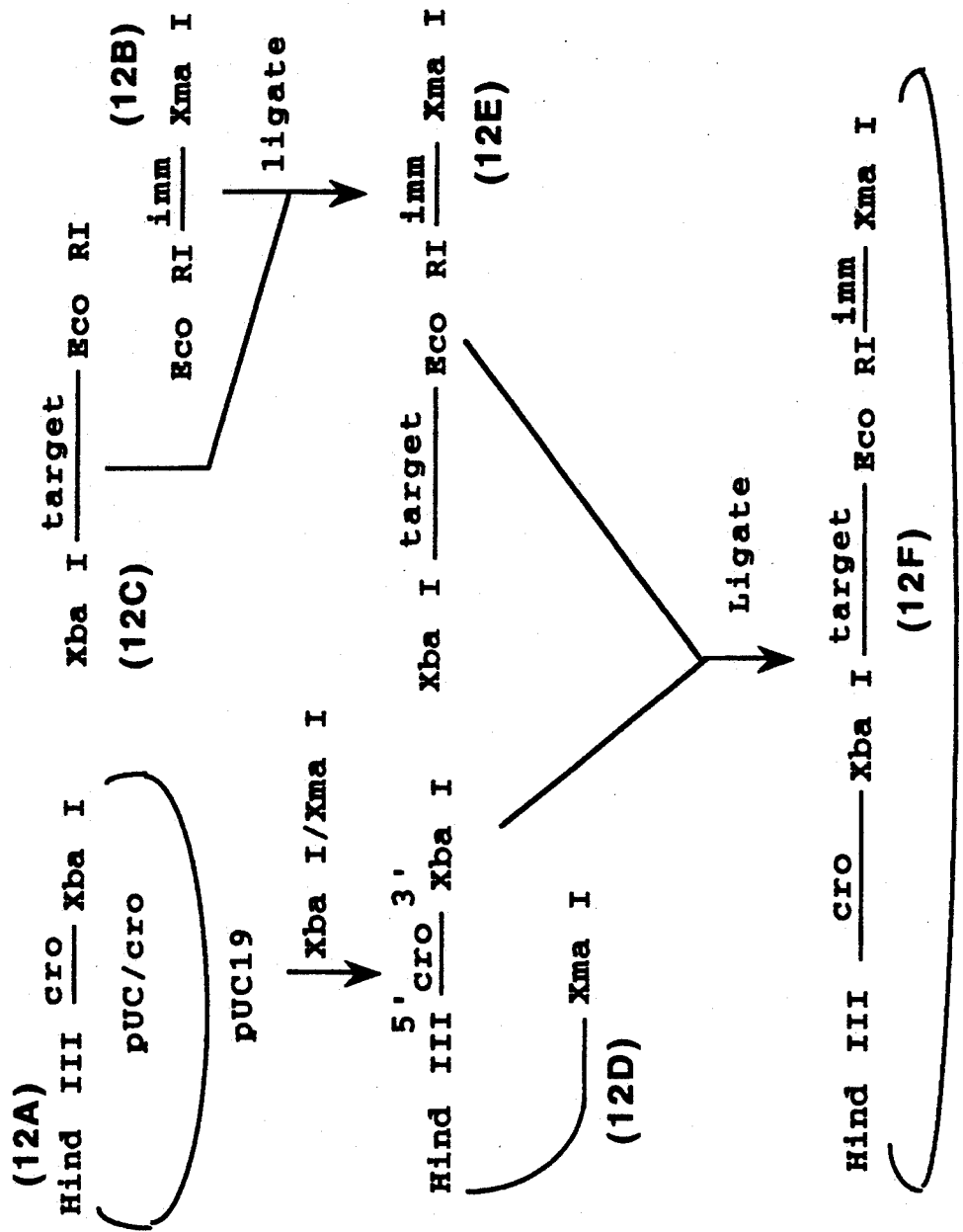
Figure 13A:
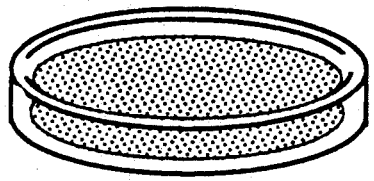
Figure 13B:
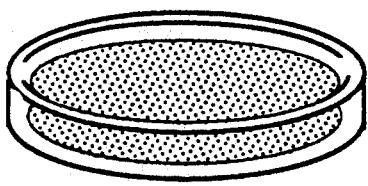
Figure 13C:
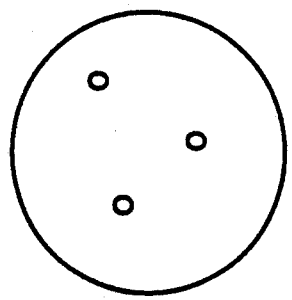
Figure 14:
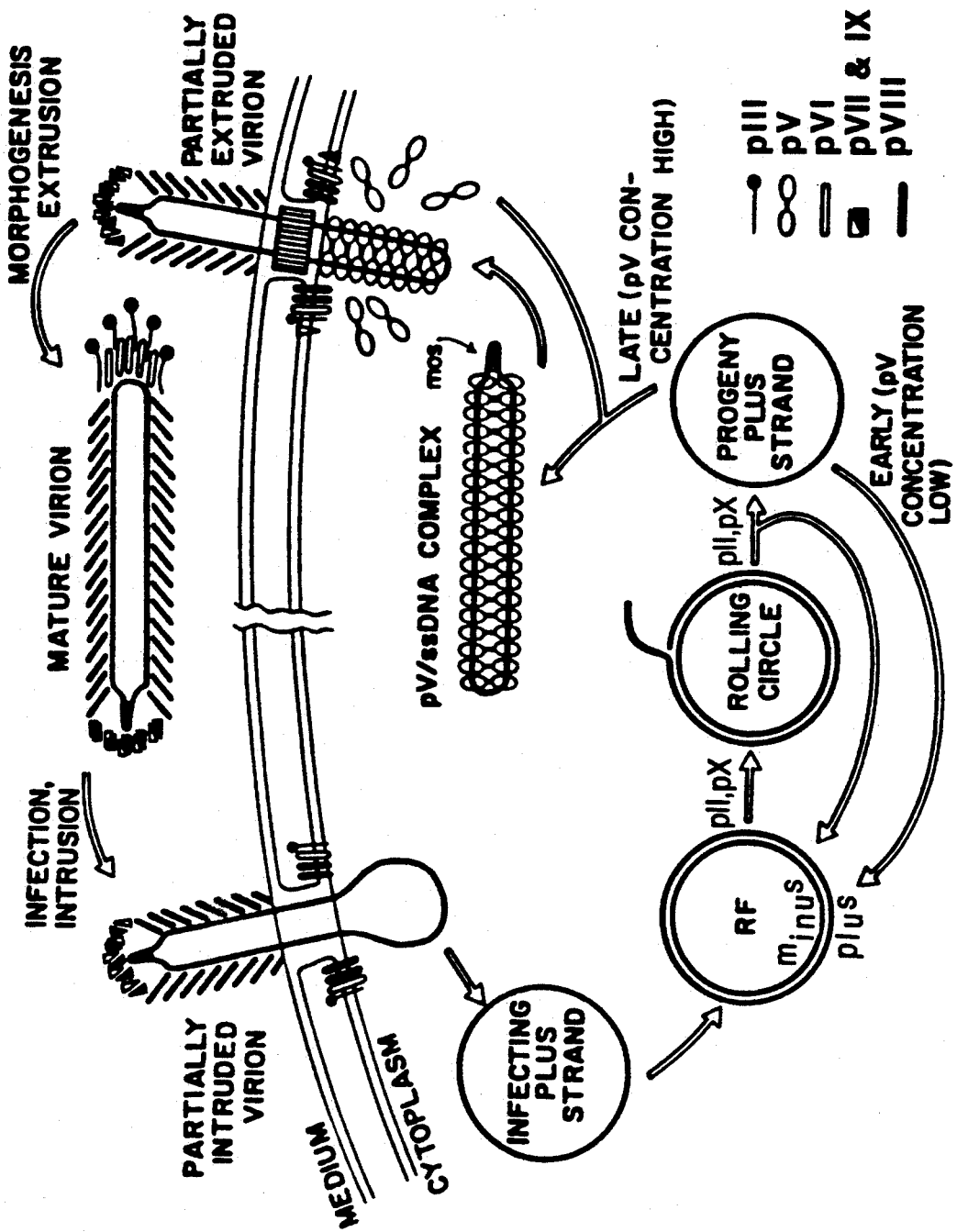
Figure 15:
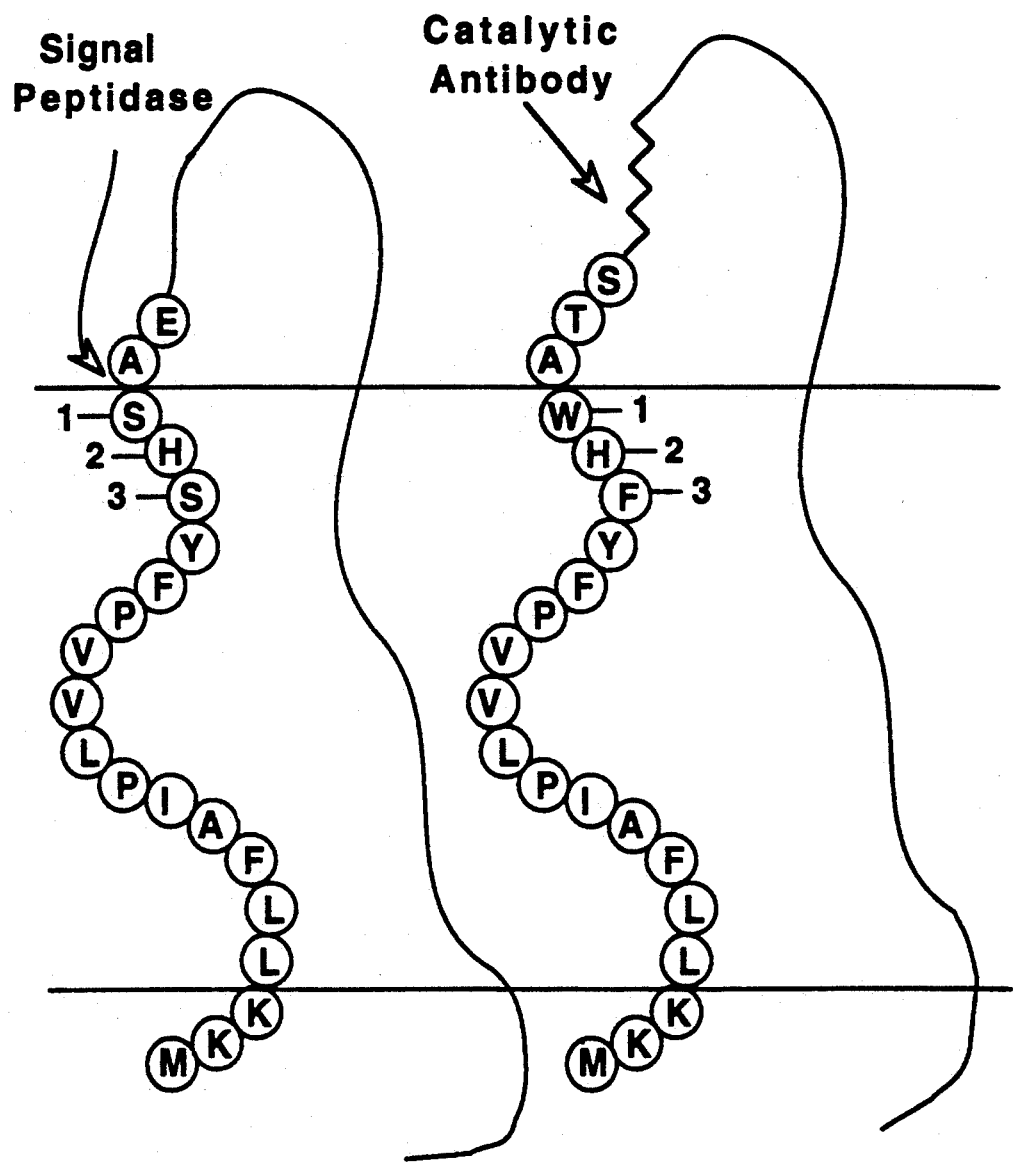
Figure 16:
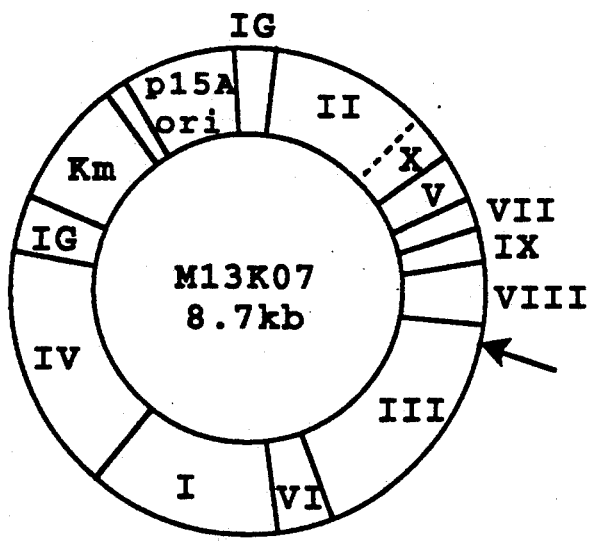
Figure 18:
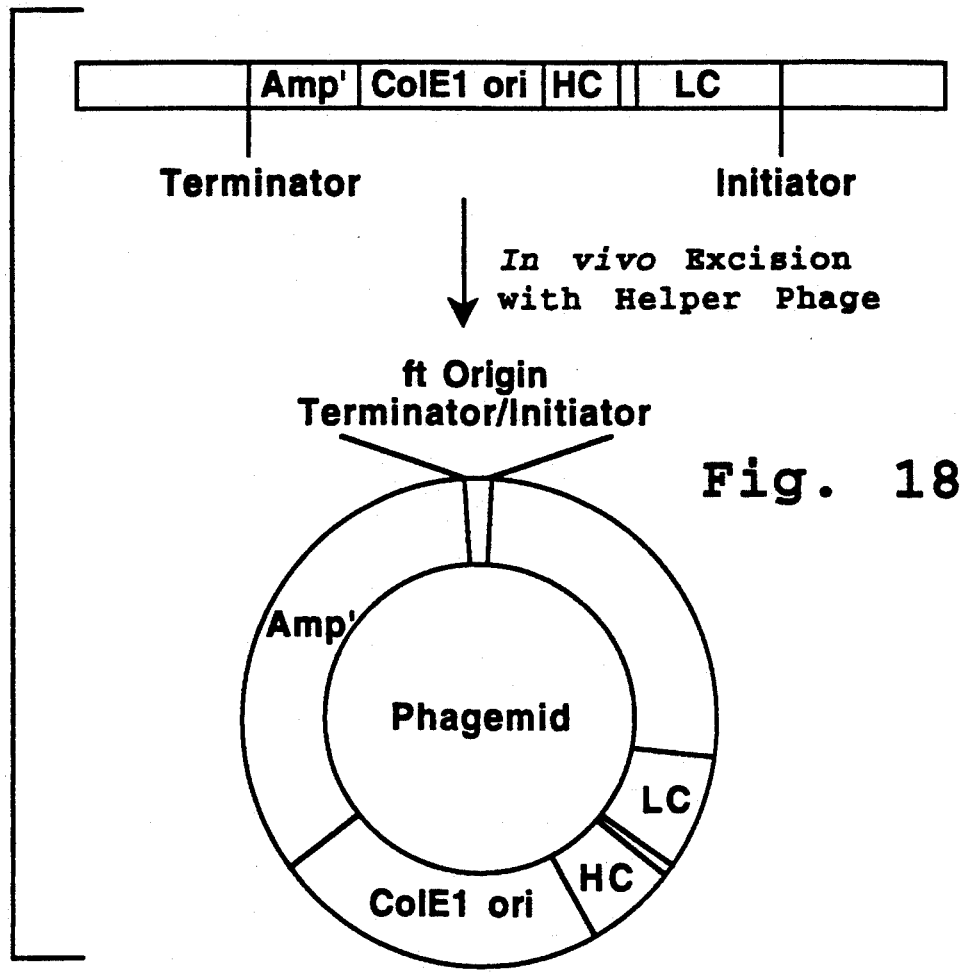
Figure 17:
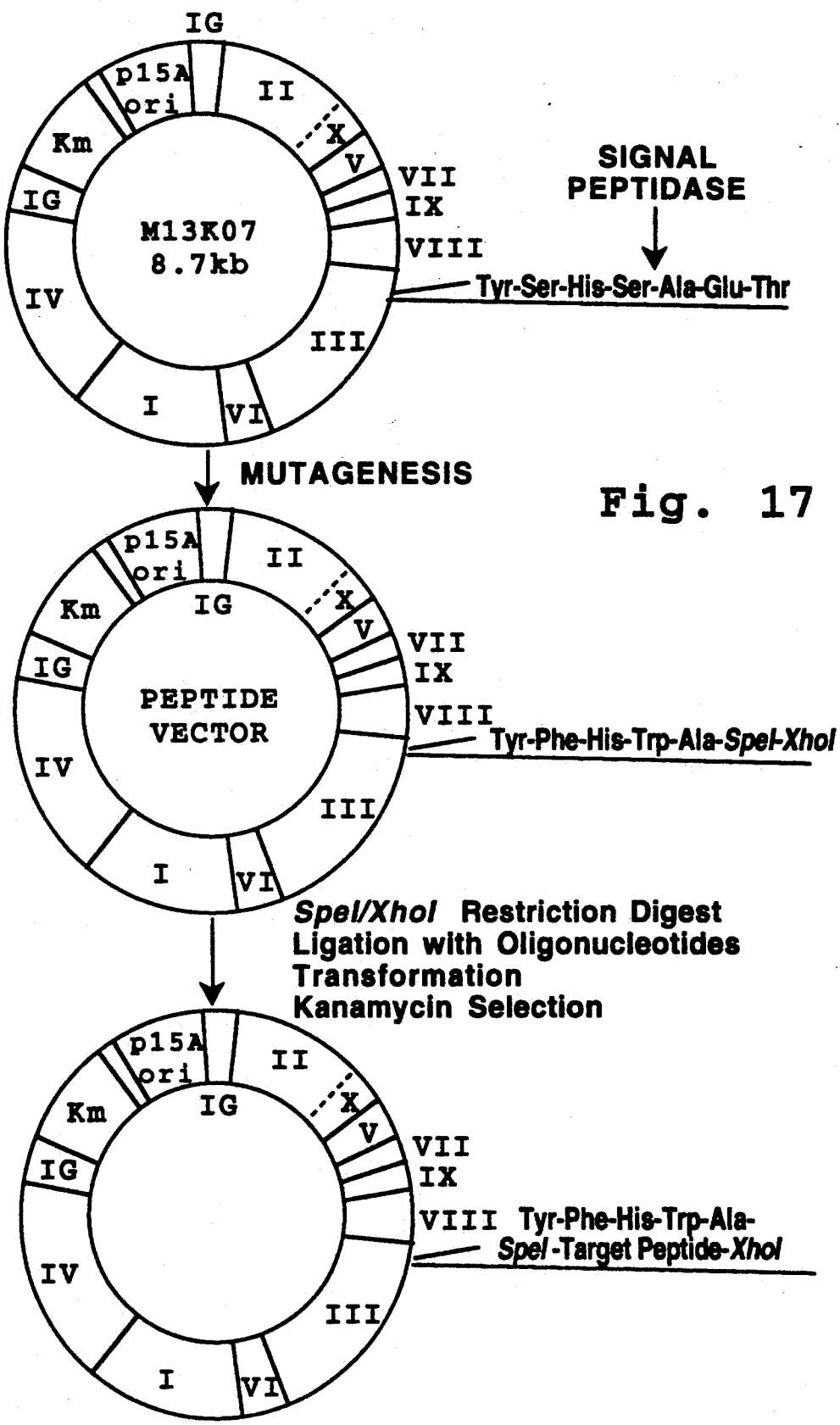
Figure 19:
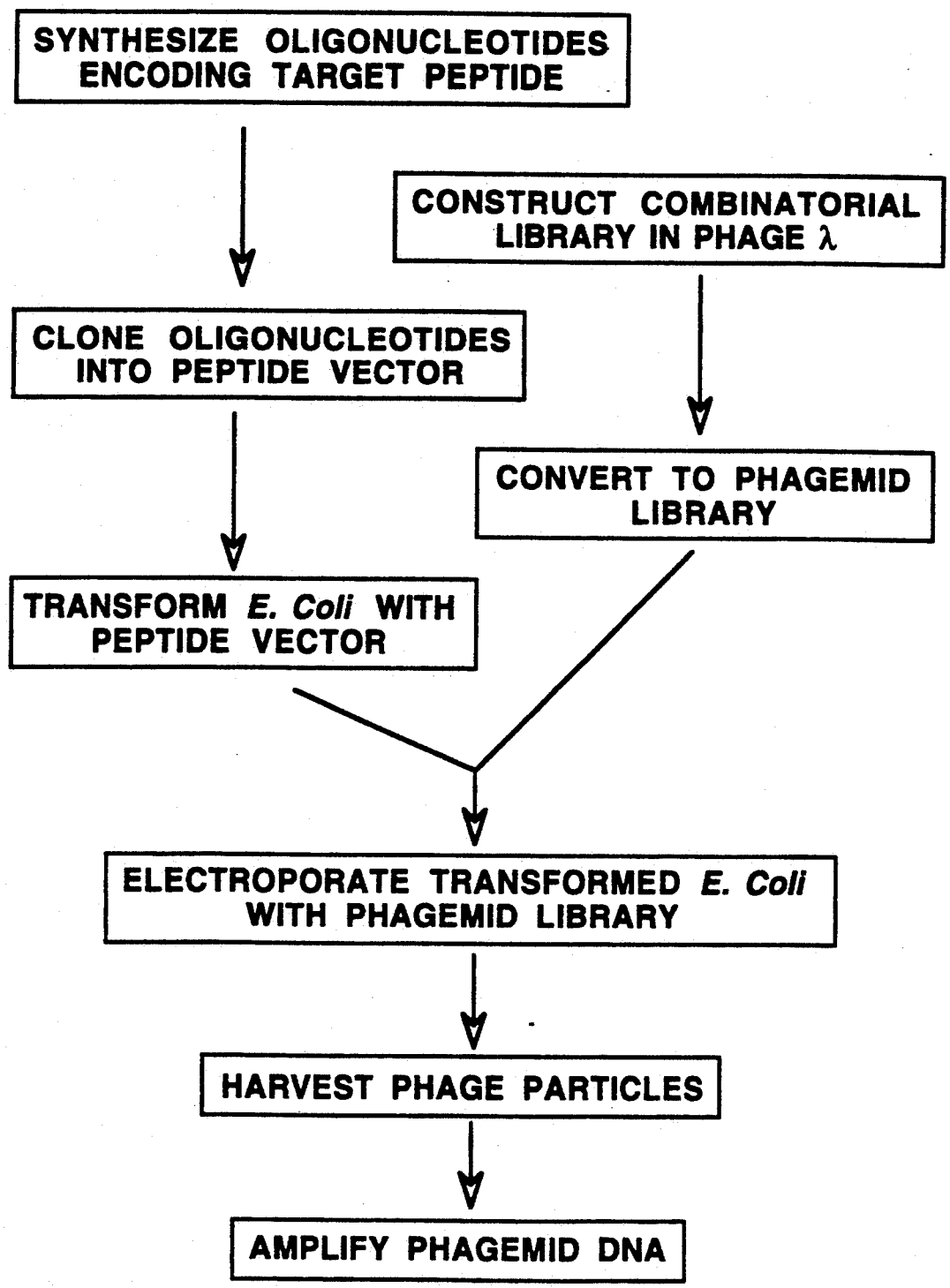

FIG. 4 illustrates the vectors used in construction of a combinatorial antibody gene library;

FIGS. 5A, 5B, and 5C illustrate an antibody matrix formed by mouse anti-rat IgG antibodies containing a target region of interest (5A) and rat anti-mouse IgG antibodies also containing the target peptide (5B), FIGS. 5C and 5D illustrate an antibody matrix formed by combining these two antibodies before (5C) and after (5D) proteolytic cleavage of the target region;

FIGS. 6A-6C illustrate a screening procedure based on clearing of overlay turbidity in a culture plate (6A). FIG. 6B shows a cross-section of the plate with the turbid overlay. FIG. 6C shows the appearance of the cleared region on the plate;

FIGS. 7A, 7B, 7C and 7D illustrate an antibody matrix formed by mouse IgG antibodies containing a target region of interest (circles) where the Fc region of the antibody is derivatized with biotin (7A) aggregated with rabbit anti-mouse IgG[F(ab')]$_2$ (7B) and cross-linked by goat anti-rabbit IgG antibodies before (7C) and after (7D) proteolytic cleavage of the target sequence in the matrix;

FIGS. 8A-8D illustrate a screening procedure based on release of biotin (B) derivatized Fc fragments from an antibody matrix in a bacterial overlay (8B) showing placement of a filter on the overlay (8A), transfer of derivatized fragments onto a filter (8C), and detection of the biotin containing fragments on the filter (8D);

FIGS. 9A-9D illustrate a screening procedure based on generation of free amine groups by exposing target peptides on a filter (9A) to colonies on a culture plate (9B), and assaying the filter (9C) for the presence of free amino termini by fluorescence groups (9D);

FIGS. 10A and 10B illustrate a target peptide blocked at one end (X) and labeled at one end with a fluorescence reporter, before (10A) and after (10B) site specific cleavage;

FIGS. 11A and 11B illustrate a target peptide labeled at its opposite ends with first and second enzymes which act cooperatively on a substrate S to generate a signal product $P_1$, through an intermediate $S_1$, before (11A) and after (11B) peptide cleavage;

FIG. 12 schematically illustrates the construction of a vector to express a fused protein composed of the lambda cro protein (12A), the colicin E1 immunity protein (12B), and the target sequence of interest (12C); 12D and 12E show, respectively, the digestion of the parent vector and insertion of the target/immunity coding sequences; 12F shows the final vector;

FIGS. 13A-13C illustrate steps in the selection of plaques producing target specific proteolytic antibodies;

FIG. 14 illustrates the infection cycle of filamentous phage;

FIG. 15 illustrates a normal gene III protein product and the protein product derived from the engineered gene III in the vector M13K07. The amino terminus of the engineered pIII can be liberated by a catalytic antibody capable of cleaving the target peptide, represented by a zig-zag line;

FIG. 16 shows a schematic of the target peptide vector. A map of M13K07 is shown and the point at which gene III has been modified is indicated by an arrow;

FIG. 17 shows details of the processes of converting M13K07 into a target peptide vector and of introducing the peptide coding sequence into the peptide target vector. In brief, site-specific mutagenesis is used to change codons −1 and −3 (FIG. 15) relative to the signal peptides cleavage site (indicated by an arrowhead) to phenylalanine (Phe) and tryptophan (Trp) respectively Mutagenesis is also used to insert sites for restriction enzymes SpeI and XhoI between codons +1 and +2. Oligonucleotides containing the indicated overhanging ends and coding sequences for the target peptide are ligated into the target peptide vector at these two restriction sites;

FIG. 18 shows the generation of the phagemid from the LAMBDA ZAP vector;

FIG. 19 shows an overview of the selection method presented in Example 6; and

Figure 20:
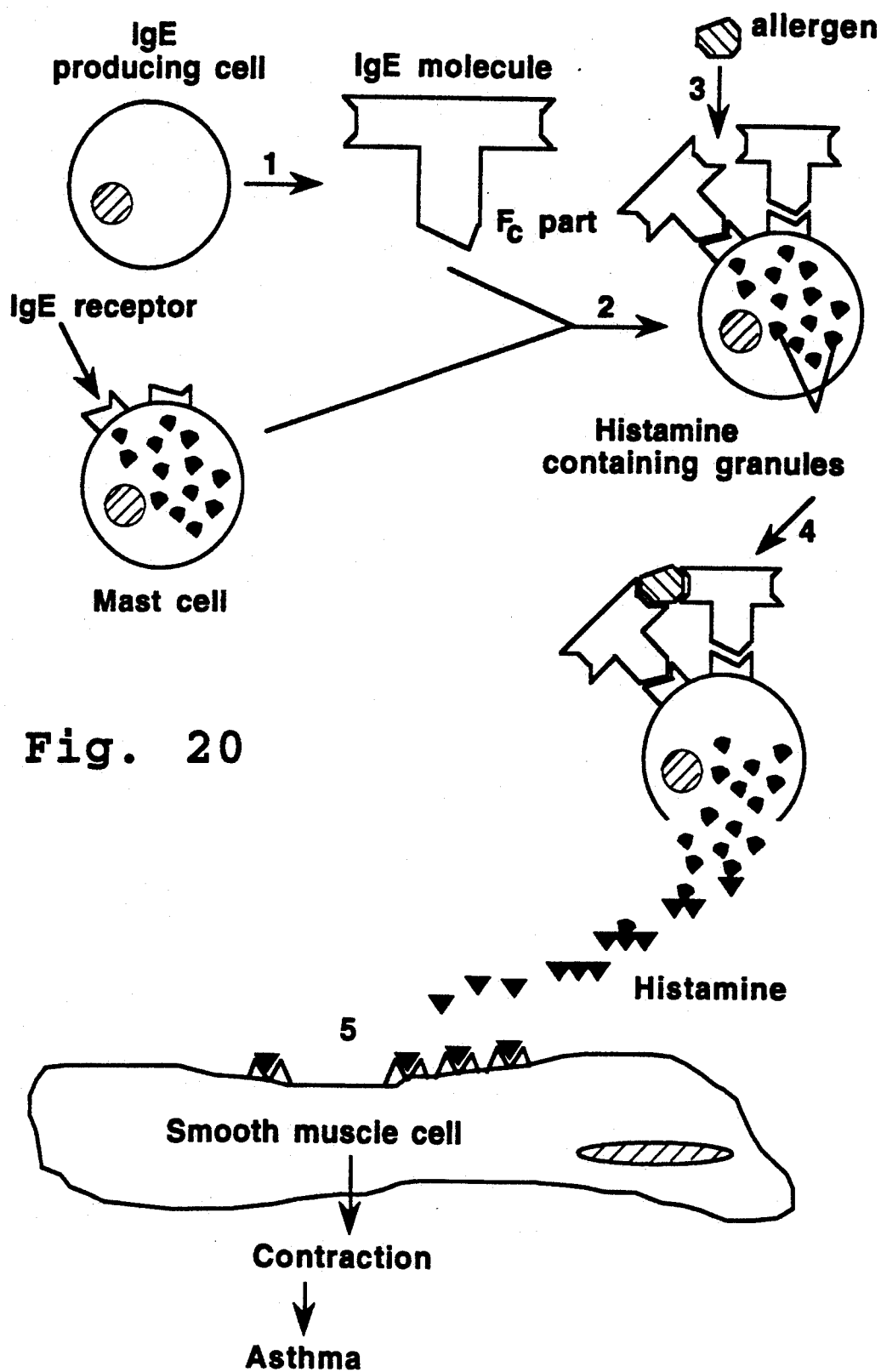

FIG. 20 illustrates schematically the IgE and allergen binding events responsible for histamine release from a mast cell in an allergic response.

6. DETAILED DESCRIPTION OF THE INVENTION

I. Preparing Proteolytic Antibodies

A. Preparing Target Peptide

The methods of the present invention can be used to generate proteolytic antibodies capable of cleaving a defined target peptide sequence: antibodies capable of such cleavage are herein called catalytic antibodies.

Generally, selection of target peptides from larger protein coding sequences only requires that the target sequence is physically accessible to cleavage. Some desirable characteristics for a target peptide include: (i) the presence of some charged amino acids; (ii) a general hydrophilic nature; (iii) a sequence long enough to allow for the desired specificity. In regard to the length of the sequence, if a catalytic antibody having specificity similar to a serine proteinase is to be isolated then the recognition sequence need only be similar to that for a serine proteinase: for example, specificity similar to elastase, the cleavage site is X-↑-Y, where X is uncharged and non-aromatic (e.g. Ala, Val, Leu, Ile, Gly, Ser) and Y is non-specific (Boehringer Mannheim, Biochemica Information). However, if more specific cleavage is desired the number of amino acids composing the target site needs to be increased.

Figure 1A:
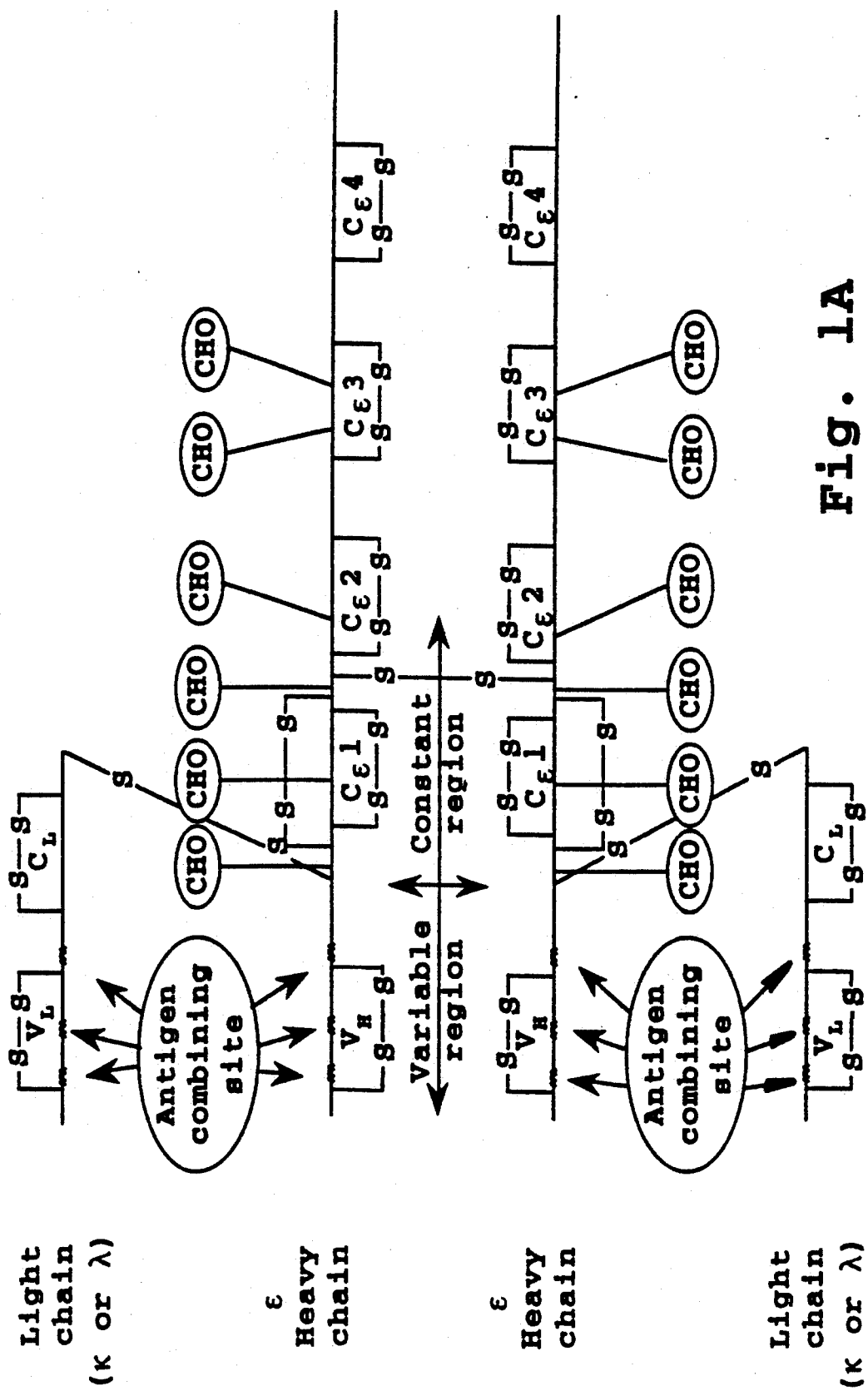
FIG. 1A shows an IgE antibody.
Figure 1B:
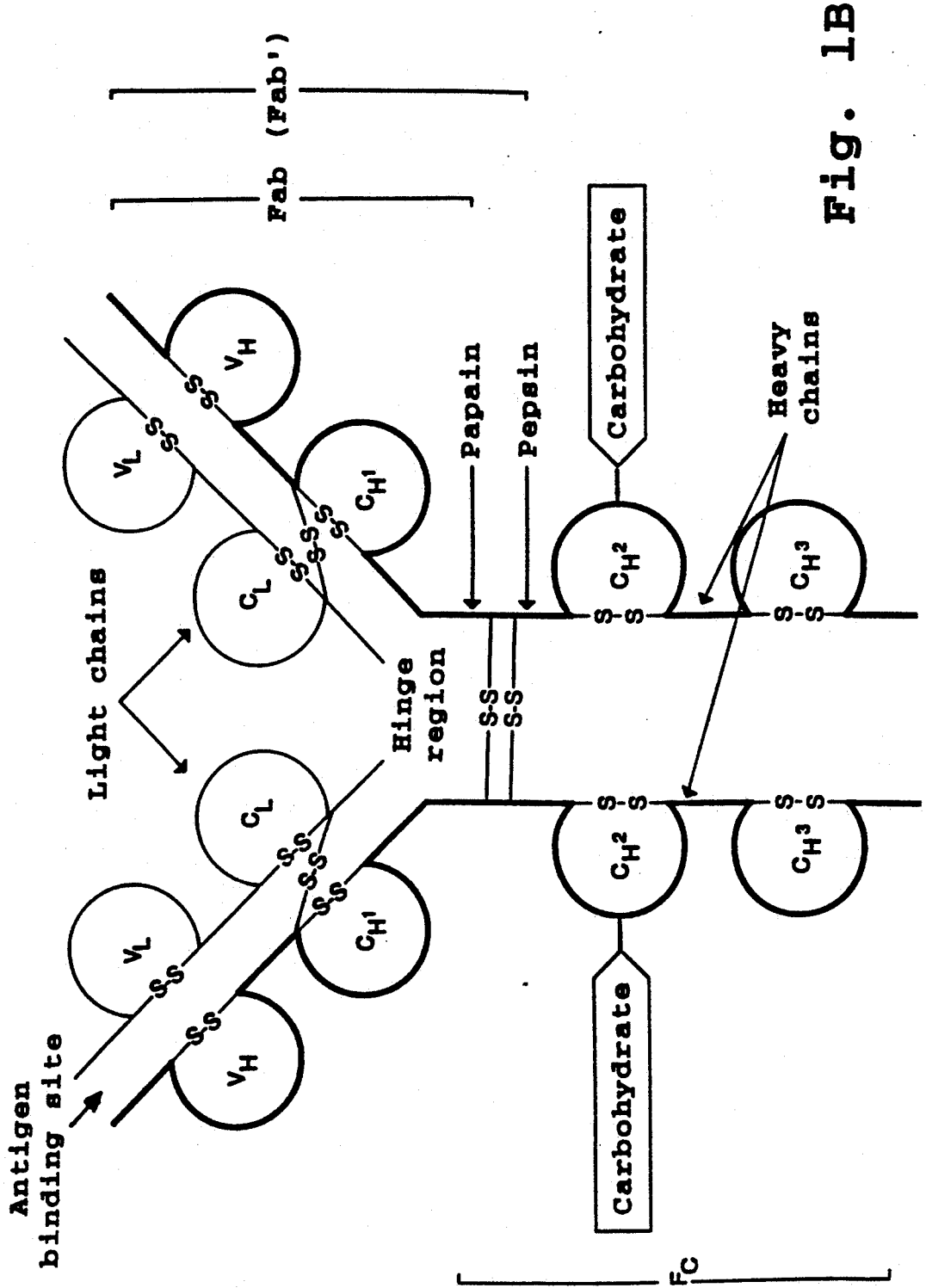
FIG. 1B shows a typical IgG antibody.

For purposes of illustration, the present disclosure describes the generation of catalytic antibodies capable of specifically cleaving human IgE molecules in a manner to separate the Fab region (the antigen binding region, FIGS. 1A and 1B) from the Fc region of the molecule which contains the FcR binding site of the molecule. The FcR binding site is the site of attachment of the IgE molecule to its receptor on cell surfaces (see section II). It has been previously determined (Helm et al, 1988) that the Fc receptor binding domain lies within residues 301–376 (see FIGS. 2 and 3). Cleavage in this region destroys receptor binding activity (Helm et al, 1988).

To select useful target sequences, the primary and secondary structure of the protein were examined. The structure of the human IgE heavy chain is illustrated in FIG. 2. As can be seen from FIG. 2 there are two areas in the constant regions of the IgE heavy chain (I and II) in which cleavage allows separation of the Fab from the FcR region, due to the locations of the internal heavy chain disulfide bridges. The amino acid sequence of these two regions is given in FIG. 3: regions I and II are underlined.

Other cut sites in the IgE molecule are potentially useful as long as the end result of cleavage is the separation of the antigen binding region from the receptor binding region. The catalytic antibodies will cleave both circulating as well as receptor-bound IgE molecules. Catalytic antibodies can also be selected which cleave circulating IgE molecules in the Fc binding regions which then prevents binding of the IgE to mast cells.

Proteins of interest can be examined for a variety of characteristics by using computer assisted sequence analysis and comparisons. For instance, a sequence can be scanned for likely target sites by searching for antigenic sites (ANTIGEN program, Intelligenetics, Mountain View Calif.; based on the method of Hopp et al.) or doing a standard hydropathicity analysis (SOAP program, Intelligenetics; based on the method of Klein et al.). Antigenic sites tend to be sites available on the surface of proteins. Further, minimum sequences that will distinguish the target protein from other proteins can be determined by sequence comparisons (e.g., using the SCANSIM program, Intelligenetics; based on the method of Needleman et al.). This approach was applied to the analysis of target region II of the IgE molecule. The ANTIGEN program identified the region containing EDSTKKCA as a likely antigenic site. This eight amino acid sequence was then compared to the protein sequences available in the SWISS-PROT data bank, using the SCANSIM program. The nearest protein was found to match this sequence at only 4 amino acid positions (KKCA). This result suggests the use of the EDSTKKCA 8-mer as a target sequence would provide both availability to cleavage and good specificity to the human IgE molecule.

B. Expressing IgE $F_{ab}$ Fragments from Library Clones

A combinatorial library of Fab fragments is generated in phage lambda essentially according to the method of Huse et al. Using this technique a large library can be screened directly by standard techniques for clones expressing antibodies of any desired specificity. This approach obviates the need for synthesizing transition states and greatly expands the possible number of antibodies. Moreover, these libraries have the potential of expressing a diversity even greater than that of the animal from which they are derived. For example, the number of different antibodies in an individual human's immune repertoire has been estimated to be on the order of $10^8$. Since the immunoglobulin cloning approach allows for random assortment and association of heavy and light chains that would not normally occur in vivo, it is anticipated that as many as $10^9$ individual clones can be obtained. Accordingly, these libraries offer the possibility of creating antibodies in vitro that do not exist in vivo, thereby increasing the spectrum of potential catalytic antibodies.

The general approach to construction of the combinatorial libraries is described in Example 1 and the required vectors are diagramed in FIG. 4. In brief, coding sequences for immunoglobulin light chains as well as the $V_H$ and $C_H1$ domains of the heavy chains are amplified in vitro from a suitable mRNA source. Suitable sources for the mRNA include B lymphocytes or plasma cells from any of a variety of tissues from any species: for example, mouse spleen cells or human peripheral blood lymphocytes. The choice of immunoglobin light chains of course depends on the species chosen as the mRNA source: for example for human, mouse, and rabbit mRNA sources, light chains are chosen from the group consisting of κ and λ chains. The sequences for the amplification primers are selected from known light chain, $V_H$, and $C_H1$ sequences (Kabat et al.). The primers are synthesized by standard oligonucleotide synthesis techniques.

The amplified products are then cloned into lambda vectors, resulting in the generation of a light chain library and a heavy chain library. Example 1 describes the creation of expression libraries using mouse γ heavy chains and mouse κ light chains. The two libraries are then crossed at a specific restriction enzyme cleavage site to generate a combinatorial Fab expressing library. The phage are packaged in vitro and then plated.

Due to the nature of the expression vector the combinatorial Fab fragments are secreted by the bacteria. Accordingly, the plated phage serve as the templates for the screening procedures described below.

The libraries are screened for the percentage of plaques which are efficiently expressing combinatorial Fab fragments by screening duplicate plaque-lift filters using two antibodies, one directed against the heavy chain and the other against the light chain. Plaques which test positive for the expression of both chains are counted as expressing the potentially useful Fab fragments.

II. Screening Procedures for Identifying Catalytic Antibodies Having Defined Sequence Specificity The above procedures allow the generation of a large number of antibody molecules which have great diversity. The next step is to provide means to identify the catalytic antibodies of interest: that is, those antibodies capable of cleaving the defined target peptide sequence. The following screens have been developed for this purpose; once again the IgE target is used as a model system.

The catalytic antibodies of interest must cleave the Fc region of the IgE molecule in such a way as to separate the antigen-binding and receptor-binding domains. The following procedures describe techniques which can be used to rapidly screen the combinatorial libraries generated above for the presence of antibodies which can cleave the IgE regions of interest.

A. Turbidity Overlay

The first screening method is based on the clearing of a turbid overlay to detect clones corresponding to catalytic antibodies of interest. In a preferred embodiment of the first screen, recombinant mouse anti-rat IgG and rat anti-mouse IgG immunoglobulin molecules are used as a vehicle for the target peptide of interest. The target peptide is inserted just above the hinge region of the IgG molecule, roughly corresponding to the papain cleavage sites indicated in FIG. 1.

The target peptide coding sequence can be either synthesized directly by standard methods of oligonucleotide synthesis, or, in the case of larger target sequences, synthesized by a combined approach of synthesis and sequential cloning (Example 2).

To screen for an IgE-cleavage specific catalytic antibody a fragment of target region I was chosen to exemplify the screen. The target region has the following amino acid sequence (in the single-letter code): ILQSSCDGGGHFPPTIQLL. The nucleic acid sequence encoding this peptide is constructed in a series of cloning steps, by generating a tandem array of multiple oligonucleotide fragments corresponding to the coding sequence of the complete target region generated. The final product is cut out of the cloning vector and the target sequence inserted into the gene encoding the heavy chain mouse anti-rat IgG clone in the region indicated in FIG. 1 as a papain cleavage site (mIgG/e). The same manipulations are carried out to insert the target sequence in a rat anti-mouse IgG (rIgG/e). These recombinant constructs are then transfected into myeloma cells to generate intact mIgG/e and rIgG/e molecules having the IgE cleavage target sequence (mIgG/e, FIG. 5A; rIgG/e, FIG. 5B).

Recombinant mouse anti-rat IgG/e molecules and rat anti-mouse IgG/e immunoglobulins are mixed into separate soft agar overlays which are maintained as liquids. To the mIgG/e mixture the rIgG/e soft agar solution is added. The first soft agar solution is titrated with the second solution until complex/aggregate formation is obtained (FIG. 5C).

The final soft agar mix is overlaid on a test plate of the phage/plaque combinatorial library (FIGS. 6A). Antibodies which cleave the target peptide sequence cause the recombinant molecules to break into three parts and thus totally disrupt the matrix (FIG. 5D). Disruption of the antibody matrix results in the formation of an easily-seen clear plaque in the otherwise turbid layer (FIG. 6C).

The majority of catalytic antibodies which cleave any of the immunoglobulin molecules at other sites will cause either partial or no disintegration of the immune complex aggregates. Therefore, these antibodies will be distinguishable from antibodies of the desired specificity.

The same sort of turbid matrix can be formed using any combination of antibodies (IgA, IgG, IgE etc) which will result in the required cross linking (e.g. FIG. 5C). Further, other methods capable of generating precipitates of proteins containing the target sequence of interest, such as heating or chemical crosslinking, are also applicable to generating the turbid overlay.

This embodiment has broad applicability as a general screening technique in that any target peptide of interest, regardless of source, can be inserted into the same site as was described for the IgE peptide.

In another embodiment of the first screening method, plates with plaques of phage producing antibodies are overlaid with an agar layer containing aggregates of IgE, making the layer turbid. Aggregation can be achieved by a variety of means. One preferred method of aggregation is crosslinking the IgE molecules with antibodies to two different IgE regions: for example, rabbit anti-humanIgE/Fc, and rabbit anti-human-IgE/-Fab. The IgE molecules themselves can either be naturally occurring IgE, as isolated from human myeloma serum (Ishizaka, et al.), or the IgE molecules can be recombinantly produced from hybridomas as ascites in mice.

B. Release of a Diagnostic Reporter

A second screening method involves the release of a diagnostic reporter from a support by cleavage of the target sequence of interest by a catalytic antibody. In this screen the target peptide is connected with a reporter molecule, such as an enzyme, biotin, or radioactive label. The target molecule is then immobilized on a support. The reporter molecule is then released when a catalytic antibody cleaves the target peptide sequence only release of the reporter molecule allows for its detection.

Example 3 describes two embodiments of the second screen utilizing release of antibody matrix-bound reporter molecule. The first method is very similar to the first screen described above, except the Fc portion of the mIgG/e and rIgG/e molecules are reporter-labelled before formation of the antibody lattice (FIG. 5C). The labelling of the Fc portion of the molecule is explained below.

Figure 7A:
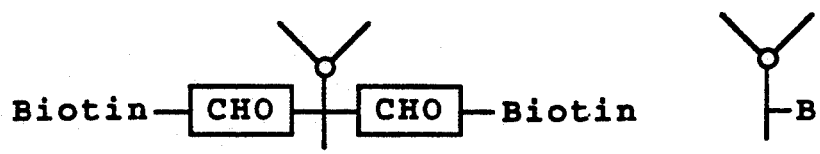

In the second method, the recombinantly produced mouse anti-rat IgG molecule is isolated (Example 2) which contains the IgE target region number I (FIG. 3) (this molecule is subsequently referred to as mIgG/e). The Fc portion of the IgG/e molecule is then labelled. A number of ways to label the Fc portion of the IgG/e molecules are available including the following: (i) an enzymatically labelled antibody or Fab fragment specific for binding to the IgG/e Fc region; (ii) direct labelling of the IgG/e molecule such as by biotinylation or radioactive labelling. Example 3 describes labelling the carbohydrate groups of the IgG/e molecules with biotin (FIG. 7A).

Figure 7B:
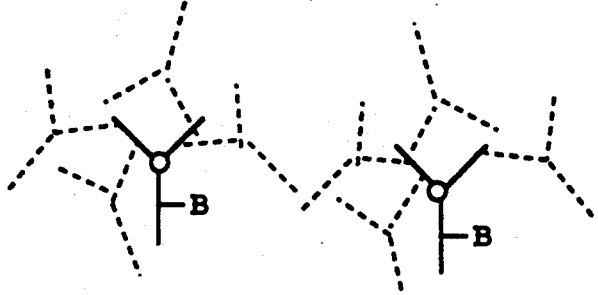
Figure 7C:
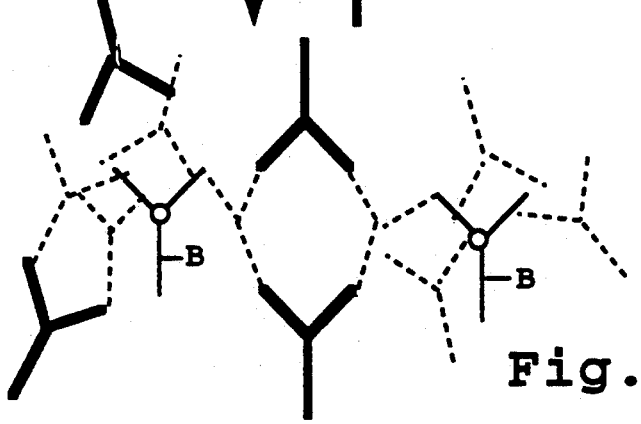

In the second method, a soft agar overlay solution is prepared containing the labelled mIgG/e and rabbit anti-mouse IgG[F(ab')]$_2$ which together form aggregates of antibody molecules (FIG. 7B). To cross link these aggregates and form the antibody matrix this solution is then titrated with the goat anti-rabbit IgG solution until a precipitate begins to form (FIG. 7C).

The soft agar solution containing the antibody matrices generated by either of the above methods is then layered over plaques (FIG. 8B) generated by the combinatorial library. A filter which is effective to bind any released reporter molecule, in this case a GENESCREEN or nitrocellulose filter, is laid on top of the soft agar (FIGS. 8A, C). The plates are placed at 37° C. and incubated overnight in a humidified incubator.

The filters are then assayed for the presence of the reporter molecule. In the present embodiment the biotin/protein complexes released from the antibody matrix, as a result of cleavage of the target sequence by catalytic antibodies (FIG. 7D), bind to a transfer filter. The presence of the protein/biotin complex on the filter is then detected by standard methods (Ausubel et al.; Pierce - Product Catalogue: FIG. 8D).

As mentioned above in the discussion of the first screening method, many combinations of antibodies can be used to generate the antibody-matrix (e.g., IgA, IgG, IgE).

In another embodiment of the second screening method a reporter molecule is linked to a filter via a target sequence bridge. The filter is layered over plaques generated by the combinatorial library. Catalytic antibodies expressed by the phage which cleave the target sequence bridge release the reporter molecule to the plate surface. The reporter is then detected either directly on the plate or by transfer from the plate to a second filter.

C. Use of Fluorescent Probes

A third screening method involves the detection of free amino groups, liberated by the catalytic antibody, using a fluorescent probe. A schematic of this method is shown in FIG. 9. The method involves coating a membrane filter with the target peptide, the amino terminus of which is blocked either during synthesis or via binding to the filter. Membrane filters are coated with the test peptide via either noncovalent or covalent binding (Example 3). If possible, lysines should be avoided when selecting the test peptide sequence. Otherwise the lysine amino groups need be derivatized such as by acetylation (K. Lubke & E. Schroder, Annalen der Chimie, 692:237 (1966). Accordingly, the preferred test peptides of the present invention (FIG. 3, underlined sequences) can be altered for this screen. In addition to the two complete test peptides, which each include at least one lysine, truncated peptides which do not include lysines can be tested, for example: from peptide I, ILQSSCDGGGHFPPTIQLL; and, from peptide II, CADSNPRGVSAYLSRPS.

Noncovalent binding of the peptide to filters (Example 3) requires that, in addition to lysine amino groups being blocked, the peptide's amino terminus is also acetylated. For covalent binding, peptides bearing a free amino terminus can easily be covalently bound to Immobilon AV membranes (Millipore) (Example 3).

Peptides can either be synthesized in vitro or recombinantly produced. For recombinant production, coding sequences for the desired peptides can be introduced into any of a number of expression vectors known to one of ordinary skill in the art. The peptide can then be recombinantly produced and isolated (Maniatis et al.; Ausubel et al.)

Another embodiment of this screen introduces a spacer molecule between the target peptide and the filter. The spacer arm permits a different presentation of the target peptide to the potential catalytic antibodies. The major requirements for the spacer molecule are that it (i) does not contain a reactive amino group, (ii) can be attached by one end to the filter, and (iii) can be attached at the opposite end to the target peptide. One such class of molecules is the group of standard spacer arms used in affinity chromatography: spacer arms suited to this purpose are widely available, for example, from Pharmacia. A prototypical spacer arm for the present application has the following structure:

The amino terminal end of the linker is attached to the filters as described for peptide amino terminal attachment (Example 3) or by, for example, CNBr activation of the amino group before reacting with the filter. The carboxyl-end is then activated by standard procedures, typically using a carbodiimide. The amino-terminal end of the target peptide is then coupled to the activated carbonyl.

When the target peptides are expressed recombinantly, sequences encoding spacer molecules, such as poly(Gly Ala Leu), can be incorporated into the expression vector. This repetitive sequence then serves as a spacer between the filter and the target peptide. Alternatively, sequences encoding multimers of the target peptide can be inserted into the expression vector. Using multimers of the target sequence reduces the likelihood of detecting irrelevant catalytic antibodies which only cleave a spacer molecule sequence and not the target sequence.

The peptide-coated filter is then overlaid on a test plate and incubated at 37° C., during which time catalytic antibodies with the desired activity cleave the bound peptide, thus generating new amino termini. The filter is then treated with a probe compound, such as a fluorescent probe (Example 3), which reacts with free amino groups and generates a color reaction. The color reaction indicates regions of the filter which show a positive reaction with the probe; the corresponding plaque generating the positive signal is then identified (FIG. 6D). This method has the advantage of being applicable to a variety of target peptides from any number of sources.

D. Two Enzyme Detection Systems

A fourth screening approach involves the use of two enzymes which serially catalyze two reactions when they are held in close proximity to each other by the target region; the target peptide functions as a linker. A third enzyme is employed in the overlay which generates a detectable product using the substrate generated by the first reaction when the above two enzymes are physically separated by cleavage of the linker.

One embodiment of this screen uses three enzymes, oxidase, peroxidase, and catalase. Briefly, the screen involves covalently attaching the oxidase ($E_1$; FIG. 11A) to the catalase ($E_2$; FIG. 11A) via a linking peptide which contains the target sequence of interest. This linking peptide holds the two enzymes in close proximity (FIG. 11A). A soft-agar overlay is formed which contains the oxidase-target-catalase complex, peroxidase, and a dye (meaning a single dye or coupled dye system) which is converted by the peroxidase, in the presence of $H_2O_2$, to a distinctively colored, signal reaction product. The peroxidase enzyme is a hydrogen-peroxide oxidoreductase, such as horseradish peroxidase, myeloperoxidase, or lactoperoxidase, which catalyses the reaction:

Donor + H₂O → oxidized donor + 2H₂O.

The specificity of peroxidase for the donor is generally low, and a number of phenols, aminophenols, diamines, and indolephenols are active. In the present invention, the donor is selected among a variety of known compounds or pairs of compounds which undergo reaction to a detectable, typically chromogenic reaction product as a result of peroxidase-catalyzed oxidation.

Exemplary donor compounds include O-phenylenediamine, amidopyrine, and naphthalene-2,3-dicarboxaldehyde. Typically formation of a colored reaction product involves dimer formation, for example 4-aminoantipyrine and 2,4,6-tribromo-3-hydroxybenzoic acid (Boehringer Mannheim).

The agar is overlaid onto the above described plates on which the phage containing the combinatorial library have been plated. In the presence of substrate for the oxidase, the oxidase reacts with the substrate ($S_1$; FIG. 11A) and generates hydrogen peroxide ($H_2O_2$). The $H_2O_2$ is then used by the catalase to convert the $H_2O_2$ ($S_2$; FIG. 11A) to $2H_2O$ plus $O_2$ ($S_3$). Cleavage of the target peptide linking $E_1$ and $E_2$ by a catalytic antibody, which is specific for cleavage of the target peptide, results in physical separation of the two enzymes (FIG. 11B). The peroxidase which is also present in the overlay then has the opportunity to convert the dye to the detectable form. The concentration of the peroxidase can be titrated to optimize reaction conditions to allow detection of the positive-dye signal.

One suitable oxidase is D-amino acid oxidase. The porcine D-amino acid oxidase has been cloned in an *E. coli* expression vector (Ciccarelli et al.). At the 3' end of the D-amino acid oxidase gene an oligonucleotide encoding the target sequence of interest is inserted in frame by standard recombinant manipulations (Ausubel et al.; Maniatis et al.). The recombinant protein is then isolated by the method of Ciccarelli et al.

For the present invention the target sequence typically may consist of either peptide I or II (FIG. 3). Further, in addition to the target sequence other extension sequences may be present to provide a longer linking peptide which helps reduce any steric complications which may inhibit availability of the target sequence for cleavage. For example, one such extension sequence encodes the polypeptide poly(Gly Leu Ala) and can be employed as follows:

(GLA)$_N$SRDFTPPTVKILQSS(GLA)$_N$C.

The carboxyterminus of the fused protein has an additional cysteine residue to allow thiol crosslinking to the second enzyme (see below). The coding sequences for the linking peptides can either be completely derived from corresponding IgE coding regions and any extension sequences added as synthetic oligonucleotides or the entire sequence can be generated synthetically (Ciccarelli et al.; Crea; Yoshio et al.).

The catalase is then derivatized using a suitable hetero-bifunctional crosslinking agent which provides for crosslinking between the thiol group of the oxidase/target fusion protein's terminal cysteine and the amino-terminus of the catalase. Suitable hetero-bifunctional crosslinking agents include the following: sulfo-m-Maleimidobenzoyl-N-hydroxysulfosuccinimide ester (sulfo-MBS); sulfosuccinimidyl(4-iodoacetyl)aminobenzoate (sulfo-SIAB); and, sulfosuccinimidyl 4-(N-maleimidomethyl)cyclohexane-1-carboxylate (sulfo-SMCC). All of the crosslinking agents listed above and their suggested reaction conditions are available from Pierce (Rockford, Ill.). For example, catalase (Boehringer Mannheim) is complexed with sulfo-SIAB at pH > 7.0. The sulfo-SIAB-NH-Catalase complex is then added to the oxidase/target fusion protein at pH = 7.5 resulting in the formation of a stable thioether bond connecting the fusion protein to the catalase.

The oxidase/target/catalase complex is then added to a soft agar overlay (Maniatis et al.) along with the dye and peroxidase (Boehringer Mannheim). The soft agar mix is overlaid on the plaques representing the combinatorial library. Where the infected bacteria are secreting a catalytic antibody which is capable of cleaving the target peptide a positive-dye signal is generated.

The relative concentration of the components is optimized to permit detection of positive plaques by titrating the positive-dye reaction using serially-diluted concentrations of peroxidase added to the soft-agar overlay. The concentration of peroxidase is optimized at the transition concentration between a confluent positive-dye signal covering a plate and no detectable positive-dye signal (in the absence of specific catalytic antibodies) on a plate.

The plaque region corresponding to a positive signal is collected, replated, and re-assayed to identify specific plaques containing phage which encode the catalytic antibody of interest.

Table I shows several exemplary substrate/oxidase combinations which can be used instead of the D-amino acid oxidase used above. Other enzymes which generate the substrate recognized by the oxidase enzyme can be included in the overlay, as long as they do not interfere with the dye-detection system. For example, cholesterol esterase can be included to convert cholesterol in esterified form to free cholesterol which cholesterol oxidase then uses as substrate to produce cholestenone and $H_2O_2$ in the presence of oxygen.

TABLE I

| Substrate | Oxidase |
|---|---|
| glucose | glucose oxidase |
| uric acid | uricase |
| amino acid | amino acid oxidase |
| cholesterol | cholesterol oxidase |
| L-glycerol-3-phosphate | L-glycerol-3-phosphate oxidase |
| sarcosine | sarcosine oxidase |

E. Using Chromogenic or Fluorogenic Substrates

A fifth screening method involves the use of analytical chromogenic or fluorogenic substrates to detect cleavage of the target peptide. This screen is based on the methods disclosed by Smith and Gargiulo et al. The target peptide of interest, such as peptide I or II (FIG. 3), is protected at its amino-terminus by derivatization using, for example, a carbobenzoxy group (Gargiulo et al.). The chromogenic or fluorogenic group is then attached to the carboxy-terminus of the target peptide (Smith; Gargiulo et al.): these compounds then serve as substrate for catalytic antibodies having proteolytic activity.

For chromogenic substrate screening a typical chromogenic group is 4-methoxy-2-naphthylamine (Smith). The peptide derivatized with the chromogenic group is added to buffer-soft agar (Jones; Jones et al.). The soft-agar is layered over the plaques representing the combinatorial library: these plates are incubated overnight at 37° C. The plates are then flooded with a diazonium salt solution (Jones; Jones et al.). In the presence of a catalytic antibody which is capable of cleaving the peptide from the chromogenic group, the chromogenic group reacts with the diazonium salt to form an azo dye. The intense color generated by the azo dye is easily visibly detected. The plaque region corresponding to the positive signal is collected, replated, and re-assayed to identify specific plaques containing phage which encode the catalytic antibody of interest.

For fluorogenic substrate screening a typical fluorogenic group is 5-aminoisophthalic acid dimethyl ester (Gargiulo et al.). As above, the peptide derivatized with the fluorogenic group (FIG. 10A) is added to a soft agar overlay. The plates are incubated at 37° C. and periodically examined on a UV light box (Fotodyne, New Berlin, Wis.) for the presence of the liberated fluorogenic group (FIG. 10B). As above, the plaque region corresponding to the positive signal is collected, replated, and re-assayed to identify specific plaques containing phage which encode the catalytic antibody of interest.

F. Use of Enzymes Containing the Target Sequence

A sixth screening approach involves selection of the target peptide sequence and searching of available protein databases to identify an enzyme containing a homologous sequence. The homologous sequence can be determined by using, for example, the PCGENE SCANSIM program (Intelligenetics, Mountain View, Calif.). The SCANSIM program searches for protein sequence similarities between a reference sequence of between 5 and 30 amino acids and a library of known protein and enzyme sequences. The program does not require exact identity and allows for some substitutions based on the Dayhoff matrix (Needleman et al.; Dayhoff et al.; Doolittle). If the protein/enzyme containing the sequence similar to the target peptide is not an exact match, it is then manipulated in vitro by standard mutagenesis techniques (Ausubel et al.; Maniatis et al.) to contain the exact target peptide sequence.

The advantages of using a protein/enzyme identified by sequence comparisons instead of the original target peptide include the following: (i) the protein/enzyme may be more readily available than the target protein of interest; and (ii) the protein/enzyme may have an easily detectable phenotype resulting from its cleavage by a catalytic antibody.

In any of the above screening methods, after regions of the test plate have been identified as positive, the plaques located in this area are removed and re-plated at a lower density. The screening is then repeated to confirm the selection of positive plaques.

III. Selection Procedures for Identifying Catalytic Antibodies Having Defined-Sequence Specificity In addition to the above screening methods, bacteria containing phage expressing a catalytic antibody of interest can also be identified by genetic selection techniques. Genetic selections offer an important advantage over screens in that conditions are provided under which only the candidates of interest are capable of growth. Accordingly, specific candidates that normally occur at low frequencies can be more easily identified by selections than by screens.

A. The First Selection Method

The catalytic antibodies of the present invention can be selected essentially as described in Example 5. First, a combinatorial library is constructed in a parent lambda vector which is genetically modified to carry a temperature conditional-defective gene which is essential to lytic development of lambda. Any number of lambda or host-specific genes can function in this capacity, for example, any of the early genes N, cro, O, P, or, Q (Gussin et al.).

In order for the present selection to work, the catalytic antibody must be able, in some way, to supply the gene product required for lytic growth under the non-permissive conditions. One embodiment of the selection requires that a wild-type copy of the conditionally-defective gene is fused in-frame to a second protein via a target sequence bridge: the target sequence is the cleavage site of the desired catalytic antibody. The second protein must in some way be able to prevent the required wild-type protein from performing its normal cellular function. The only way to generate the wild-type protein required for lytic growth is to cleave the fusion protein in the target region and liberate the wild-type protein. There are several ways to disable the wild-type protein including the following: (1) proteins which function in complexes are fused to second protein sequences which interfere with complex formation; and, (2) sequestering of the gene product away from its normal site of action. Disablement of the wild-type protein is effected by the second protein component of the fusion. The mere presence of an amino or carboxy terminal extension may, in some cases be enough to disable the wild-type protein. However, the disabling effect of the second protein is exacerbated by, for instance, choosing an extremely hydrophobic protein coding sequence to fuse to the required wild-type protein. In this case the fused proteins will be directed by the hydrophobic second protein region to either membrane associate or cluster in a manner similar to micelle formation. Cleavage of the target sequence bridge by a catalytic antibody frees the required wild-type protein to perform its function in the lytic cycle, thus leading to the generation of viable phage and plaque formation. In the absence of cleavage, i.e. no required wild-type protein is available, there is no plaque formation. Another advantage of using a hydrophobic second protein is that due to the hydrophobic nature of the protein less of its sequence is presented as substrate to possible cleavage by the antibodies.

One particularly useful lambda gene appropriate for use in the present selection is the cro gene (Gussin et al.). The cro protein functions as a dimer to regulate early transcription of the lambda genome. Accordingly, the cro protein must bind DNA and interact with another cro protein. Cro protein function is required for lytic development. There are many conditional mutations available in the lambda cro gene which can be used in the present selection. For example, suppressible amber mutations in the cro gene can be made temperature conditional by having the host *E. coli* strain carrying a temperature-sensitive tRNA suppressor (for example, Hussain et al.). If a lambda phage carrying an amber mutation in the cro gene is transfected into a plating strain of *E. coli* which has a temperature-sensitive tRNA amber suppressor, the phage will be able to form plaques at 32° C. but not at 42° C. The phage is otherwise wild-type, i.e. it does not require the presence of supE for growth. The mutant parent phage are generated by standard genetic manipulations or, alternately, by site-directed oligonucleotide mutagenesis. The generation of the combinatorial library in the modified lambda vector is outlined in Example 5A.

Example 5B describes one application of the above described selection. The coding sequence for the cro gene product is modified by standard procedures to have terminal HindIII (5') and XbaI (3') adapters (Example 4B, FIG. 12A). This sequence is cloned into the polylinker of, for example, the pUC19 vector. As a second protein the coding sequence for the 113 amino acid inner membrane protein colicin E1 immunity (colE1 imm) is selected (Goldman et al.). The coding sequence is modified to have terminal EcoRI and XmaI adapters at its 5' and 3' ends respectively (FIG. 12B). The synthetic target sequence (ILQSSCDGGGHFP-PTIQLL: Example 2) is cut out of the pUC19 vector with XbaI and EcoRI restriction enzymes (FIG. 12C).

The pUC/cro vector is doubly-digested with XbaI and XmaI (FIG. 12D). The target sequence and colE1 imm coding sequence are ligated into the vector resulting in an in-frame fusion between the cro protein, the target region, and the colE1 imm protein (pUC/cro/-mem; FIG. 12E, F).

The pUC/cro/mem vector is then introduced into a lambda plating strain containing a temperature-sensitive amber repressor. Transformants are selected which have the characteristic ampicillin resistance of the pUC19 vector. Any number of cloning vectors, known to one of ordinary skill in the art, can be used for these standard cloning manipulations. One useful modification is to introduce the fusion protein coding sequence into, for example, an F' plasmid (Mieschendahl et al.) which eliminates the requirement of a drug selection to maintain the fusion protein coding sequences in the bacterial plating strain. Alternatively, the fusion construct is introduced into the bacterial genome. Different bacterial promoters may be utilized to increase or decrease the level of fusion protein production depending on the construct of choice.

A cloned plating strain containing the coding sequences for the protein fusion of interest used to plate the combinatorial library described in Example 5A. The plating efficiency of the library is tested at the permissive temperature and the phage stock diluted to yield the following final per plate concentrations of plaque-forming units: $10^7$, $10^8$, $10^9$ (FIG. 13A). These plates are then incubated at a temperature which is non-permissive for lytic growth (FIG. 13B) unless the required wild-type protein, cro, is liberated from the fusion protein construct. The plates are then examined for the presence of plaques (FIG. 13C).

In addition to identifying the catalytic antibodies of interest, the selection may also pick up real or pseudo-reversion of the temperature conditional-sensitive cro gene. To distinguish between these possibilities, plaques are picked and transfected into the following two plating strains: (i) a bacterial strain lacking the pUC/cro/-mem vector; and, (ii) a bacterial strain carrying pUC/-cro/mem vector. Phage able to generate plaques in the absence of the pUC/cro/mem vector clearly do not depend on the fusion protein encoded by the vector to provide wild-type cro function. On the other hand, phage which generate plaques only in the presence of the pUC/cro/mem vector are selected for further analysis.

The specificity of the selection can be increased by using conditional mutations in two genes essential for lytic development. Any genes chosen for this selection from the lambda genome can be easily manipulated in vitro since the entire sequence of the lambda genome is known. Lambda has the further advantage that many types of conditional mutations are available, including suppressible-lethal mutations and temperature sensitive mutations. For instance, the above selection which utilizes the cro gene can be coupled with a second conditional mutation in Nu1. Nu1 is required for proper cleavage of the lambda genome for packaging. This cleavage function is performed by the phage terminase enzyme which is a complex formed between the Nu1 protein and the A protein.

A number of amber mutations are available in the Nu1 gene (Weisberg et al.). The amber-Nu1 mutation is introduced in the parent phage as described above for the cro mutation. For convenience the parent phage can be passaged in a normal suppressor bearing host (such as a SupE bearing strain). A nucleic acid sequence encoding a Nu1-target bridge-second protein fusion is generated. Both of the fusion protein coding sequences are then introduced into the plating host bacterial strain which carries a temperature-sensitive tRNA amber suppressor. The combinatorial library is then plated as described above.

Alternatively, the cro and Nu1 proteins can be fused to each other by a target bridge peptide. Generation of viable phage which can generate plaques requires cleavage of the bridge peptide only since the cro and Nu1 peptides must remain intact to result in a productive lytic infection.

The second protein sequence of the fusion protein can be any number of membrane proteins or shorter hydrophobic sequences. In some cases highly charged peptides as the second protein may more effectively interfere with the required wild-type gene function.

B. The Second Selection Method

The second selection method of the present invention also provides for the selection of catalytic antibodies capable of cleaving a defined peptide target sequence. In the method, bacteria are infected with a defective helper-phage that can only support propagation of infectious phage particles if a protein essential for phage production is cleaved at a particular target site. A combinatorial library encoding Fab fragments is expressed on a phagemid independently introduced into the same host bacteria. This antibody library is the source of potential catalytic antibodies capable of cleaving the target site. Insertion of a specific peptide into the cleavage site imposes specificity on this selection scheme.

One embodiment of this selection scheme is described in Example 6. Gene III in the filamentous phage cloning vector M13K07 (an M13-based phage; Vieira et al.) encodes a minor coat protein called pIII (FIG. 16). Four to five copies of pIII are inserted into the coat of each phage particle (Smith 1988). pIII mediates binding to the F pilus protein of *E. coli* and in this role is essential for fruitful infection (Nelson et al.). The pIII protein is produced in a precursor form for export to the periplasmic space where phage particles are assembled. For production of useful pIII protein, the export sequence, which directs the protein to the periplasmic space, must be cleaved by a sequence specific peptidase.

FIG. 14 illustrates the infection cycle of the M13 phage. The mature virion is drawn to emphasize the stoichiometry and locations of the minor virion proteins of M13 but greatly under-represents the major virion protein pVIII,* and to protrude into the periplasmic space.

For use in the present screen, gene III is altered to destroy the signal peptidase cleavage site (FIG. 15) and to introduce a convenient cloning site for insertion of peptide coding sequences. This modified phage vector is referred to as the peptide vector (Example 6). Sequences encoding any number of potential target peptides can be inserted in this site.

The peptide vector is co-transformed with a phagemid combinatorial expression library (Example 6, Figure ) into a host bacterial strain. Transformation can be accomplished by a number of standard methods including electroporation (Ausubel et al.). In the absence of cleavage of the defective pIII peptide, phage particles assemble and are secreted, but are not infectious. Because M13K07 carries a kanamycin-resistance determinant, bacteria transformed with the vector can be selected and stably maintained.

In cells transformed with both the peptide vector and the antibody-encoding phagemid (FIGS. 4, 18, and 19), the two constructs have the potential of helping each other. The peptide vector contains all the genes necessary for phage assembly and can therefore help package antibody-encoding phagemid DNA into phage particles. In turn, if the antibody-encoding phagemid carries the gene for a catalytic antibody capable of cleaving the target peptide, it can restore pIII function and, as a result, infectious phage particles are generated. As stated above, pIII is known to protrude into the periplasmic space: the periplasmic space is also known to be the location of antibody assembly (Better et al., Skerra et al.).

After a suitable incubation period, infectious phage recovered from the media will contain either the peptide vector or antibody-encoding phagemids, which bear genes encoding antibodies of the desired specificity and proteolytic capability. The phagemid genomic DNA will predominately be incorporated into phage particles as a result of the properties of M13K07 that favor packaging of phagemid DNA over packaging of its own DNA (Vieira et al.). The phage will provide plaques only when both the phagemid vector (encoding the appropriate catalytic antibody) and the M13K07 vector are present in the same cells.

The above-described selection methods are easily adapted for use with any target peptide sequence of interest.

FIG. 14 illustrates schematically the IgE and allergen binding events responsible for histamine release from a mast cell in an allergic response.

IV. Specificity Testing

After the initial identification of candidate phage encoding catalytic antibodies of interest using the above screening and selection procedures, the specificity of the catalytic antibodies is tested.

Plasmids are generated from the LAMBDA ZAPII vectors to facilitate purification of the catalytic antibodies (Example 6A). The specificity of the isolated catalytic antibodies is tested as follows. First, human IgE molecules are subjected to cleavage by each isolated catalytic antibody. The aliquots of the cleavage products are separated by SDS-PAGE and then transferred to nitrocellulose membranes and probed with a rabbit anti-human IgE antibody conjugated to alkaline phosphatase. Alternatively, the IgE can be radioactively labelled or biotin labelled by standard procedures. Specific cleavage of the human IgE molecules by a catalytic antibody in the target region of interest results in two bands on SDS-PAGE under non-reducing conditions.

When a candidate catalytic antibody generates the predicted cleavage fragments, the cleavage fragments are isolated by HPLC, or other chromatographic separation techniques, and are N-terminal sequenced to specifically define the cleavage site of the antibody. The sequence recognition specificity of the catalytic antibody is further investigated by generating a number of variations of the target peptide sequence, with amino acid substitutions throughout the target region. These targets are then examined for their ability to function as substrate: a specific cleavage sequence or set of sequences for each antibody is generated from this data.

If a catalytic antibody obtained by any of the above selection or screening methods is not of sufficiently high affinity for the target substrate, the substrate affinity may be increased by recombining the heavy chain with the entire light chain library: conversely, the light chain with the entire library of heavy chains. The libraries thus generated are screened, by any of the above methods, for new antibodies with higher affinities. A second approach to generating increased affinity is to perform saturation mutagenesis of the complementarity determining region of the antibody and to screen the mutants for higher affinity binding.

Also, the specificity of the catalytic antibody cleaving only the IgE molecule and not other proteins, i.e. selectivity, is tested. To examine selectivity, the catalytic antibodies of the present invention can be used to digest heterogeneous protein samples to see if they have activity against other serum or cellular proteins. For example, serum proteins or mast cell lysates are treated with an IgE-cleaving catalytic antibody. The products of these catalytic antibody treatments are then resolved on two-dimensional protein gels (Ausubel et al.) as are the components of the corresponding untreated samples. The treated and un-treated samples are compared to identify protein cleavages resulting from the presence of the catalytic antibody. As a positive control samples can be doped with IgE before treatment with the catalytic antibody. Sensitivity of this test can be increased by either radioactively labelling the sample proteins (e.g. by iodination or metabolic labeling) or by use of Western blotting techniques (Ausubel et al.).

II. Allergy Treatment Method

IgE is one of nine classes of immunoglobulins which are distinguished by their Fc domains, with all molecules within a class having an identical Fc region. The allergic response begins when an individual produces antigen-specific IgE antibodies in response to certain antigens (step 1, FIG. 14). The IgE molecules bind to IgE/Fc-specific receptors, i.e., receptors specific for the Fc region of IgE antibodies, on the surfaces of mast cells, which are fixed in certain tissues, and basophilic granulocytes, which circulate in the blood (step 2, FIG. 14). When multivalent allergen binds to and thereby crosslinks the cell surface-bound IgE molecules (step 3, FIG. 14), the cells degranulate (step 4, FIG. 14). This process results in the release of certain mediators, such as histamines, which in turn cause the allergic symptoms in the target organ, e.g., bronchospasm in asthma, or edema in a local allergic reaction (step 5, FIG. 14).

The present invention provides for a variety of screens and selections to identify proteolytic antibodies specific for the cleavage of two peptide regions in the human IgE molecule (FIG. 3). Cleavage of either of these regions separates the Fab region of the IgE molecule, which is responsible for binding of multivalent antigens which lead to cross linking of the IgE molecules, from the Fc region of the IgE molecule, which is responsible for binding to mast cells and basophilic granulocytes. Accordingly, exposure of IgE molecules which are bound to their receptor cells to the proteolytic antibodies of the present invention results in cleavage of the IgE molecules and, consequently, a blocking of the allergic reaction.

A. Systemic Treatment Methods

Systemic treatment methods using the catalytic antibodies of the present invention are useful as preventative therapy for allergies. For example, parenteral administration of an IgE-cleaving catalytic antibody will significantly reduce the level of IgE present in the serum. Accordingly, in the absence of IgE, the allergic response, described above, will not be initiated.

The catalytic antibodies of the present invention are formulated for parenteral administration in a suitable inert carrier, such as sterile physiological saline solution, sterile dextrose 5% in water for injection, or sterile dextrose 5% in normal saline. The dose to be administered is determined by what is pharmaceutically effective. A pharmaceutically effective dose is defined as a dose effective to produce significant reduction in the level of IgE and/or an easing of the physiological effects of allergen bound to IgE.

B. Nasal or Inhalation Treatment Methods

Inhalation provides an effective means for delivery of a variety of therapeutic compounds, including nasal decongestants and drugs useful in the treatment of asthma and other bronchial/pulmonary conditions. An advantage of inhalation therapies in treating nasal, bronchial and pulmonary conditions is that the drug is delivered directly to the site of drug action. Another advantage is the rapid onset of the therapeutic effect as compared to parenteral administration.

Cross (1986) has pointed out that allergic asthma is almost certainly the result of release of mast-cell-derived mediators into the airway microenvironment. Further, it is probable that mast cell mediator release is involved in other forms of asthma as well, for example, exercise-induced bronchospasm. Accordingly, inhalation therapy using the catalytic antibodies of the present invention is an effective route of delivery to stop the progression of such adverse bronchial conditions: cleavage of IgE molecules on the surface of the mast cells will block release of the mast cell mediators.

Several methods are well known in the art for delivering therapeutics by inhalation. In one method, the catalytic antibody is dissolved in a suitable solvent which can be aerosolized to form a small-particle mist. The protein-containing solution may be aerosolized by pneumatic or ultrasonic nebulizer, or, more conveniently, by means of a self-contained nebulizer containing a pressurized, fluorocarbon propellant. Inhalation of the aerosol mist, i.e., drawing the mist from the mouth or nose into the respiratory tract, acts to deposit the therapeutic-containing aerosol particles on various sites of the respiratory tract, including the upper nasopharyngeal region, the tracheobronchial region, and the pulmonary region.

Also well known in the prior art are inhalation systems in which a therapeutic is administered in particulate form, either as a dry powder or as a micronized suspension in a suitable carrier solvent system. Typically the catalytic antibody is dissolved in an aqueous solution and suspended in micronized form in a fluorocarbon-type propellant solvent. Following aerosolization, most of the propellant solvent is lost through flash evaporation and replaced by moisture in the respiratory tract, leading to the deposition of hydrated micronized particles.

Both types of inhalation systems mentioned above are based on delivery of the catalytic antibody in a free form to sites in the respiratory tract. As such, the protein is rapidly utilized. Micronized particles slow the release of the proteins but micronized particles may irritate the respiratory tract. One method of providing both immediate and long term respiratory tract release of catalytic anti-bodies is liposome encapsulation of the proteins. Liposome inhalation systems for administering therapeutics to the respiratory tract in liposome-entrapped form have been described (e.g., Radhakrishnan et al.). One advantage of liposome encapsulation is that un-encapsulated protein present in the liposome suspension is immediately available in the respiratory tract: the encapsulated protein is more slowly released thus providing longer term treatment from a single dosing.

The catalytic antibodies of the present invention can also be dissolved or suspended in solution for use in simple squeeze-bottle atomizers for treatment of the nasal passages. Likewise, the upper respiratory tract can be treated using a standard pump or pressurized oral inhaler.

C. Advantages of the Treatment Method of the Present Invention

The products of IgE degradation resulting from proteolytic attack by the catalytic antibodies of the present invention are unlikely to be harmful, since IgE is normally broken down in the natural course of events. Further, as mentioned above, IgE constitutes only a minute segment of total serum: serum levels of IgE are in the range of 200 nanograms per milliliter, as compared to 12 milligrams per milliliter for IgG and 1 milligram per milliliter of IgM. Accordingly, only extremely low doses of catalytic antibodies should be required to neutralize the circulating IgE. Unlike conventional antibodies, which function by binding antigen at a 1:2 molar ratio, catalytic antibodies can degrade many antigen molecules in their lifetime and are therefore needed only in low amounts which are typical of enzymes.

The first antibody library will be made from human spleen, but spleens from other species may be screened subsequently. If only human antibodies are administered, the immune response should be negligible, since they are self-proteins which should not be recognized by the immune system. Some response to allotypes (genetic variants) or idiotypes (the specific binding region) may occur, but these responses should be of low magnitude due to the low concentration of catalytic antibodies administered. In the event that high-activity antibodies are found only in species other than human, the variable regions of these antibodies can be grafted onto human constant and framework regions (Morrison et al.).

The following examples illustrate various methods for producing target peptides and complexes containing the target peptide, and for selecting catalytic antibodies effective to cleave the peptide. The examples are intended to illustrate, but not limit, the invention.

EXAMPLE 1

Generation of an Immunoglobulin Combinatorial Library

A. Combinatorial Library

A combinatorial library of Fab fragments is first generated in phage lambda essentially as described by Huse et al. The general approach is outlined in FIG. 1. In brief, DNA coding sequences for immunoglobulin light chains as well as the $V_H$ and $C_H1$ domains of the heavy chains are amplified by polymerase chain reaction (Mullis) using, as substrate, mRNA isolated from one of the following sources: (i) naive (unimmunized) mouse spleen cells; (ii) human peripheral blood lymphocytes; or, (iii) mouse spleen cells obtained from mice which have been immunized with the IgE target region of interest (i.e. Peptide 1 or Peptide 2). The sequences for the amplification primers are selected from known light chain, $V_H$, and $C_H1$ sequences (Kabat et al.). The primers are synthesized by standard oligonucleotide synthesis techniques.

The LAMBDA ZAP II vector (Stratagene, LaJolla Calif.) is modified as described by Huse et al. to generate two vectors containing two asymmetric restriction sites, e.g. NotI and EcoRI sites, a ribosome binding site, and a secretion signal sequence derived from the bacterial pelB gene (Better et al.; Skerra et al.). The amplified products are then cloned into the modified LAMBDA ZAP II vectors (Stratagene, LaJolla Calif.), resulting in the generation of a light chain library and a heavy chain library (FIG. 1).

The two libraries are then digested with EcoRI. Further, the left arm of the light chain library and the right arm of the chain library are cleaved into small fragments by digestion with MluI and Hind III, respectively. The light chain-containing and heavy chain-containing fragments are then recombined (Maniatis et al.) to generate a combinatorial Fab expression library. A Stratagene GIGA-PACK GOLD Packaging Extract Kit is used to package the LAMBDA ZAP II clones. After packaging, the phages are diluted to the desired density of 30,000 phage per 150 mm plate. The media is rich, such as LB+0.2% maltose or NZYM+0.2% maltose (Maniatis et al.). The plating bacteria are *E. coli* strain XL-1 Blue. Isopropylthiogalactoside (IPTG) is added to the soft-agar bacterial suspension (Maniatis et al.) immediately before plating.

B. Detecting Expressed Antibodies from Plated Cells

A lower dilution of the above combinational library, 500 plaques per plate, is plated and duplicate plaque lifts to nitrocellose are generated. The filters are then immunoscreened (Ausubel et al.) using antibodies against the above-amplified light and heavy chains (for example, anti-mouse kappa chain). The plaques are then scored for the frequency of phage which co-express the light and heavy-chain proteins.

EXAMPLE 2

Screening for Proteolytic Antibodies: Turbid Overlay Method

In this example, a combinatorial Fab expression library is screened for the presence of a catalytic antibody that cleaves immunoglobulin of the IgE class in such a way as to separate the antigen binding domain from the Fc receptor binding domain. The screen involves overlaying plaques generated from the combinatorial library with an agar layer containing aggregates of IgE, making the layer turbid.

The target peptide used as substrate is derived from the epsilon heavy chain domain C$\epsilon$2 (see FIG. 3). The substrate sequence for this example corresponds to amino acid residues 235-253 in the epsilon heavy chain (Region I; FIG. 3): the amino acid sequence of this region in the single-letter code is ILQSSCDGGGHFP-PTIQLL. The nucleic acid sequence encoding this peptide is synthesized as complementary oligonucleotides with overhanging cohesive ends for cloning in-frame into the polylinker region of pUC19 (Bethesda Research Laboratories). In a series of cloning steps, a tandem array of multiple oligonucleotide fragments corresponding to the coding sequence of the complete target region is generated. This overall cloning strategy to generate synthetic genes is well known in the art (Crea; Yoshio et al.; Eaton et al.). The final product is cut out of pUC19 with XbaI and EcoRI restriction enzymes, sites for which flank the multiple cloning site in pUC19.

The excised fragment encoding the target peptide is then inserted in frame at corresponding restriction sites (i.e. XbaI/EcoRI) into two separate plasmids. One plasmid contains the cDNA for the heavy chain of a mouse anti-rat IgG$_{2b}$ monoclonal antibody. This antibody is of the mouse IgG2b isotype and is produced by a hybridoma designated RG7/11.1 (ATCC Deposit No. TIB 174; American Type Culture Collection, 12301 Parklawn Dr., Rockville Md.). The second plasmid contains the cDNA for the heavy chain of a rat anti-mouse IgG$_{2b}$ monoclonal antibody. This antibody is of the rat IgG$_{2b}$ isotype and is produced by a hybridoma designated as 7D2.1.4.5 (ATCC Deposit No. HB 92). These cDNAs are modified by standard techniques of site-specific oligonucleotide-directed mutagenesis to contain tandem EcoRI and XbaI restriction sites inserted in the IgG molecule in the region of codon 210: this region approximately corresponds to the section of the antibody protein molecule just above the hinge region. The plasmids bearing the mouse anti-rat IgG + target peptide (mIgG/e) and rat anti-mouse IgG + target peptide (rIgG/e) constructs are then transfected into myelomas expressing the corresponding light chains. The resulting recombinant antibody-secreting myelomas are each separately injected into the peritoneal cavity of mice primed with pristane to induce ascites tumors, thus generating milligram quantities of the two recombinant antibodies.

In order to form a turbid layer, the two recombinant antibodies are separately mixed with low-melting-point agarose (Bethesda Research Laboratories) in a solution containing 150 mM NaCl, 10 mM HEPES, pH=7.4, kept at 55° C. One agarose/antibody solution is then titrated with the other until immune complex formation is observed (FIG. 5), as evidenced by the combined solution becoming turbid.

The final mix is overlaid on a test plate (FIG. 6A) of the combinatorial library (Example 1). The soft agar solidifies forming a turbid layer on a test plate (FIG. 6B).

The plates are incubated at 37° C. Antibodies which cleave the target peptide sequence cause the recombinant molecules to break into three parts and thus totally disrupt the lattice, resulting in the formation of an easily-seen clear plaque in the otherwise turbid layer (FIGS. 5D and 6C).

Plaques which test positive for the production of catalytic antibodies are plaque purified and re-tested by the above assay.

EXAMPLE 3

Screening for Proteolytic Antibodies: Released Reporter Method

In this example, the combinatorial Fab expression library (Example 1) is screened for the presence of a catalytic antibody that cleaves immunoglobulins of the IgE class in such a way as to separate the antigen binding domain from the Fc receptor binding domain. The screen relies on the release of a detectable reporter upon cleavage of an IgE specific sequence by a catalytic antibody.

Matrix Formation Method A

The recombinantly produced mouse anti-rat IgG + target peptide (mIgG/e) and rat anti-mouse IgG + target peptide (rIgG/e) generated in Example 2 are isolated as described. The carbohydrate groups of the antibodies are labelled using the carbohydrate biotinylating reagent Biotin Hydrazide (Pierce, Rockford Ill.) by the method of O'Shannessy et al. In order to form an antibody matrix, the two recombinant antibodies are separately mixed with low-melting-point agarose (Bethesda Research Laboratories) in a solution containing 150 mM NaCl, 10 mM HEPES, pH=7.4, kept at 55° C. One agarose/antibody solution is then titrated with the other until immune complex formation is observed, as evidenced by the combined solution becoming turbid (FIGS. 5A, B, and C).

Matrix Formation Method B

A recombinantly produced mouse anti-rat IgG molecule is isolated (Example 2) which contains the IgE target region number I (FIG. 3) coding sequence inserted in the corresponding region of the IgG molecule (this molecule is subsequently referred to as IgG/e). The resulting IgG/e molecule is isolated and the carbohydrate groups labelled using the carbohydrate biotinylating reagent Biotin Hydrazide (Pierce, Rockford Ill.) by the method of O'Shannessy et al. A soft agar overlay is prepared (Maniatis et al.) using low melting point agarose (Bethesda Research Laboratories, Gaithersburg Md.). The soft agar overlay contains 10 mM HEPES, pH=7.5, and 150 mM NaCl. The IgG/e is added to the liquid soft agar overlay. To this mixture rabbit anti-mouse IgG[F(ab')]: (Pierce) is added in an approximately 4-fold excess (FIGS. 7A and B). The mixture is gently stirred over low heat.

A second soft agar solution (10 mM HEPES, pH=7.5, and 150 mM NaCl) is prepared containing goat anti-rabbit IgG (Pierce). The mixture is gently stirred over low heat.

After approximately 10 minutes of mixing the IgG/e-containing solution is titrated with the goat anti-rabbit IgG solution until a precipitate begins to form (FIG. 7C).

The Screening Method

The soft agar solution, generated by either Method A or B) is then layered over plates on which the combinatorial library has been plated (FIG. 8B).

The soft agar overlay is allowed to solidify. A GeneScreen filter (New England Nuclear), wetted in 10 mM HEPES, pH=7.5, and 150 mM NaCl, is layered over the soft agar (FIGS. 8A and C). The plates are placed at 37° C. and incubated overnight in a humidified incubator.

Figure 7D:
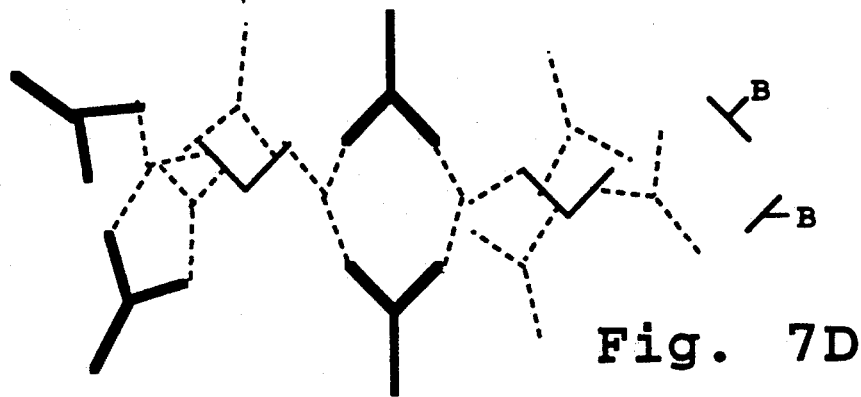
Figure 9A:
Figure 9B:
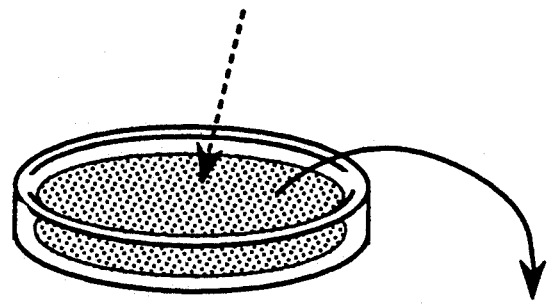
Figure 9C:
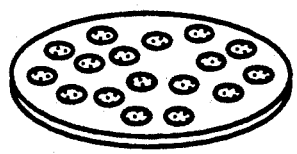
Figure 9D:
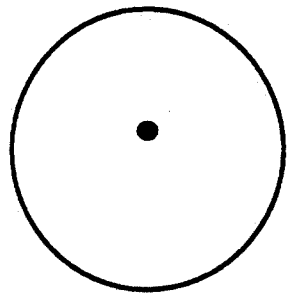

The filters are then removed and briefly washed in 50 mM phosphate buffer, pH=7.0. The filters are then assayed (FIG. 8D) for the presence of biotin/protein complexes (Ausubel et al.; Hsu et al.) which have been release from the antibody matrix as a result of cleavage by catalytic antibodies (FIG. 7D and 5D).

After regions of the test plate have been identified as positive, the plaques located in this area are removed and re-plated at a lower density. The screening is then repeated to confirm the selection of positive plaques.

EXAMPLE 4

Screening for Proteolytic Antibodies: Free Amine Fluorescence Method

In this example, the combinatorial Fab expression library (Example 1) is screened for the presence of a catalytic antibody that cleaves immunoglobulins of the IgE class in such a way as to separate the antigen binding domain from the Fc receptor binding domain.

The target peptide used as substrate is the same as described in Example 2 having the following amino acid sequence: ILQSSCDGGGHFPPTIQLL. The peptide is synthesized by standard in vitro techniques (Applied Biosystems, Foster City Calif.) and bound to filters either covalently or noncovalently.

If the peptide is to be bound noncovalently, it is synthesized with an acetylated amino terminus. GeneScreen filters (New England Nuclear) are coated with the acetylated target peptide by soaking in 50 mM phosphate buffer, pH 7.0, containing 10mM peptide for one hour. The filters are then washed briefly in 50 mM phosphate buffer.

For covalent binding, peptides bearing a free amino terminus are covalently bound to Immobilon AV membranes (Millipore) by soaking the filters in phosphate buffer containing the peptide (as above). The filters are then thoroughly washed in phosphate buffer to remove all unbound peptide.

After the covalently-bound and non-covalently-bound filters are prepared they are soaked in a solution containing 1 mM IPTG, 1 mM diisopropylfluorophosphate, and 1 mM O-phenanthrolene.

Each peptide-coated membrane filter is overlaid on a test plate and incubated for eight hours at 25° C.: the filters are marked with India ink to allow orientation to the plate after they are removed. The filters are taken off the plates and washed extensively using 0.2M sodium phosphate, pH 7.5. Finally, the filters are washed in 0.4M borate buffer, pH 8.0, and sprayed with any of the following reagents:
1) 0.2% fluorescamine in acetone
2) orthophthaldehyde reagent (25 mg. OPA in 625 μl methanol and 3.6 ml 0.4M borate buffer, pH 8.0)
3) 0.1% dansylchloride in acetone.

These reagents detect free amino groups, which indicate cleavage of the target peptide. Plaques corresponding to reactive spots on the filters are isolated and plaque purified by replating, and retested by the above screen.

EXAMPLE 5

Selection of Catalytic Antibodies Capable of Peptide Sequence Specific Target Cleavage

A. Construction of the Combinatorial Library

A combinatorial library is constructed and plated essentially as in Example 1 with the exception that the parent lambda vector is genetically modified to carry a temperature conditional-defective cro gene (see Detailed Description). The parent phage is otherwise wild-type, i.e. it does not require the presence of supE for growth. The mutant parent phage are generated by standard genetic manipulations (Arber et al.; Davis et al.; Hubacek et al.; Maniatis et al.; Miller et al.) or by site-directed oligonucleotide mutagenesis (Ausubel et al.). The library is tested as in Example 1 for expression of FAB fragments.

B. Construction of the Cro-Protein-Fusion Bearing Plasmid

The coding sequence for the cro gene product (Roberts et al.; Ovchinnikov et al.) is modified by standard procedures to have terminal HindIII (5') and XbaI (3') adapters (Maniatis et al.). This sequence is cloned into the poly-linker of the pUC19 vector (Bethesda Research Laboratories) in-frame to the β-galactosidase coding sequences. This vector, pUC/cro is transformed into E. coli and the amplified plasmid purified (Maniatis et al.).

The nucleic acid sequence encoding the 113 amino acid colicin E1 immunity (colE1 imm) protein is isolated (Goldman et al.; Oka et al.; Yamada et al.; Sutcliffe et al.) and modified by standard procedures (Maniatis et al.) to have terminal EcoRI and XmaI adapters at its 5' and 3' ends respectively. Further, the 3' adapter includes two in-frame translation termination codons. The synthetic target sequence (ILQSSCDGGGHFPPTIQLL) generated in Example 2 is cut out of the pUC19 vector with XbaI and EcoRI restriction enzymes. The pUC/cro vector is doubly-digested with XbaI and XmaI. The target sequence and colE1 imm coding sequence are then ligated into the vector resulting in an in-frame fusion between the cro protein, the target region, and the colE1 imm protein (pUC/cro/mem). The nucleic acid sequence of the cro/target/imm read through region is confirmed by standard procedures (Sequenase: TM, U.S. Biochemical Corp., Cleveland Ohio) using universal and known sequence primers.

The pUC/cro/mem vector is transformed (Maniatis et al.) into a lambda plating strain containing a temperature-sensitive amber repressor (Hussain et al.). Transformants are selected and cloned on the basis of ampicillin resistance (Maniatis et al.). A cloned amp$^R$ plating strain is inoculated for use as the lambda plating strain for the combinatorial library described in Example 5A. The bacteria are plated to media (Arber et al.; Maniatis et al.) containing ampicillin. The plating efficiency of the library is tested at 32° C. Appropriate dilutions of the phage stock are then plated to yield the following final per plate concentrations of 32° C.-plaque-forming units: $10^7$, $10^8$, $10^9$. These plates are then incubated at 42° C.

Plaques are generated by (i) real or pseudo-reversion of the temperature conditional-sensitive cro gene, or (ii) presence of a catalytic antibody capable of liberating the wild-type cro protein from the cro-target-imm protein complex. To distinguish between these possibilities, plaques are picked and transfected into a normal plating strain, i.e. lacking the pUC/cro/mem vector, and into the plating strain + pUC/cro/mem (amp$^R$). Phage able to generate plaques in the absence of the pUC/cro/mem vector, i.e. phage able to generate plaques on both bacterial strains, are eliminated as being either real or pseudo-reversion of the temperature conditional-sensitive cro gene. Phage whose ability to generate plaques are dependent on the presence of the pUC/cro/mem vector are selected for further analysis.

EXAMPLE 6

Method II for the Selection of Catalytic Antibodies Capable of Peptide Sequence Specific Target Cleavage

A. The Peptide Vector

The peptide vector is derived from M13K07 (Vieira et al.). Useful features of M13K07 are the following: (i) it carries all the genes necessary for M13 phage morphogenesis; (ii) it carries a mutated gene II, the product of which interacts with the phage origin of replication to initiate production of single-stranded DNA; (iii) it carries a disrupted phage origin of replication; (iv) it has a plasmid origin of replication; and (v) it carries a kanamycin resistance gene.

The combination of an inefficient phage origin of replication and an intact plasmid origin of replication favors propagation of M13K07 in the host bacterium as a plasmid (as RF, replicating form, DNA) rather than as a phage. It can therefore be maintained without killing the host. Furthermore, possession of a plasmid origin means that it can replicate independent of the efficient phage-like propagation of the phagemid. By virtue of the kanamycin resistance gene, M13K07 can be amplified which in turn increases packaging of phagemid DNA into phage particles.

The peptide vector of the present invention is generated as follows. Codons -3 and -1 relative to the signal peptidase cleavage site of gene III are modified: codon -3 from a serine to a phenylalanine and -1 from a serine to a tryptophan (FIG. 15). The sequence of gene III is known (VanWezenbeck). The modification of these codons is accomplished by standard procedures (Ausubel et al.). Each of these substitutions independently prevents signal peptidase recognition (von Heijne). Accordingly, a reversion of two mutations would be required to restore cleavage of the signal peptide.

Further, unique SpeI and XhoI sites are inserted between positions +1 and +2 relative to the signal peptidase cleavage site (FIGS. 16 and 17). The SpeI/XhoI restriction sites allow the directional cloning of oligonucleotides encoding target peptides of choice. The addition of foreign sequences to the amino terminus of the mature gene III protein product does not interfere with its ability to generate infectious particles (Parmley et al., Scott et. al., Devlin et al.).

B. Cloning a Target Peptide Into the Peptide Vector

The target peptide is selected from the protein that is the target for cleavage. The length of the peptide should be approximately four to twenty amino acids.

Two oligonucleotides are synthesized. One oligonucleotide, the sense strand which provides a continuous open reading frame in-frame with the gene III protein, contains, in the 5' to 3' direction, the nucleotides of SEQ ID NO:1 followed by the coding sequence for the peptide. The second oligonucleotide, the anti-sense strand, contains, in the 5' to 3' direction, the nucleotides of SEQ ID NO:2 followed by the reverse complement of the peptide coding sequence. The two oligos are annealed in a reaction mixture containing 1.0 picomole of each oligo.

One tenth of this reaction, corresponding to 0.1 picomole of the double-stranded oligonucleotide, is ligated with 1 picomole of the peptide vector RF DNA cut with SpeI and Xho I. The one to ten ratio of insert to vector promotes the cloning of a single insert per vector. Alternatively, the insert oligonucleotide may be dephosphorylated using Calf Alkaline Phosphatase (Maniatis et al.).

An appropriate strain of *E. coli* (e.g. MV 1184 or MV 1190, Vieira et al.) is transformed with the ligation mix (Maniatis et al.). Kanamycin-resistant colonies are selected. These colonies are screened by hybridization (Ausubel et al.) with an oligonucleotide corresponding to SEQ ID NO:1 or SEQ ID NO:2 that has been end-labelled with $^{32}P$.

Small scale plasmid preparations (Sambrook et al.) of double-stranded DNA are made from the kanamycin resistant colonies that test positive by hybridization. The isolated plasmid DNA is then sequenced across the peptide cloning site to ensure that (i) a single copy of the oligonucleotide encoding the target peptide has been inserted, and (ii) a continuous open-reading frame exists through the target peptide encoding sequence and the gene III coding sequences.

C. Generation of a Phagemid Combinatorial Library

A combinatorial library phagemid vector is generated in Lambda ZAP vector, available from Stratagene. These M13-based plasmids carry the fd origin of replication and are referred to as phagemids since they have both phage and plasmid-like properties (FIG. 18).

A combinatorial library of immunoglobulin genes is generated essentially as described in Example 1. The single fragments containing the light and heavy chain genes are cloned into the phagemid vector 3' adjacent the lacZ promoter thus generating a combinatorial Fab expressing library in an M13 based vector. A phagemid is excised from each vector of the combinatorial library (FIG. 18) (Short et al.; as per Lambda ZAP II manufacturer instructions).

D. Electroporation of Phagemid Combinatorial Library

The phagemid combinatorial library is introduced into *E. coli* transformed with the peptide vector by electroporation (Maniatis et al). Electroporation is much more efficient than standard transformation procedures and allows one to generate libraries of over $10^8$ independent clones (Cwirla et al.). Typically, electroporation is performed with approximately 80 ml of cells and 4 μg of DNA and using a 5 millisecond pulse of 12.5 kV/cm. The cells are then grown in L broth containing kanamycin (25 μg/ml) overnight at 37° C.

E. Harvesting and Propagating Infectious Phage

Phage particles are recovered from the overnight incubation by standard procedures (Maniatis et al.) In brief, the media is centrifuged at 12,000×g for five minutes. Phage particles are precipitated by adding one quarter volume of 2M NaCl/20% polyethylene glycol, incubating on ice for 15 minutes, and then centrifuging at 12,000×g for five minutes at 4° C.

Only a minute fraction of the phage particles recovered will be infectious, but most of these will contain phagemid DNA encoding catalytic antibodies of the desired specificity. These are recovered by coinfection of *E. coli* strain MV 1184 with M13K07 (Vieira et al.). Sufficient single stranded phagemid DNA can be prepared from individual plaques for further analysis.

EXAMPLE 7

Cloning and Specificity Testing of Catalytic Antibodies

A. Plasmid Cloning from the LAMBDA ZAP II Vectors

Catalytic antibodies are identified by one of the methods described above in Examples 2 to 6. The corresponding plaques are plaque purified and re-tested as described above. Upon confirmation of a positive result the catalytic-antibody-containing region of the LAMBDA ZAP II clones are excised and expression plasmids generated as previously described (Short et al.).

The plasmids containing genes encoding catalytic antibodies are separately transformed into *E. coli*. The single clones of the plasmid bearing bacteria are inoculated into 5 ml of L-broth (Maniatis et al.) for overnight cultures. Three mls of the overnight culture are inoculated into 500 ml of L-broth and grown at 37° C. for 4 hours (Huse et al.). Synthesis of the catalytic antibody is induced by the addition of IPTG to a final concentration of 1 mM. The culture is then incubated at 25° C. for 10-12 hours. The cultures are harvested and the cells removed by centrifugation. The remaining media, containing the secreted catalytic antibody is concentrated by ultrafiltration using Amicon filters). The concentrate is then size-fractionated using a TSK-G4000 column. The catalytic antibody containing fractions are identified by screening the fractions by ELISA assays (Ausubel et al.) using a goat antibody specific against the $C_H1$ domains of the heavy chains used to generate the combinatorial library (Example 1).

B. Specificity Testing

Human IgE molecules are isolated by standard procedures (Ishizaka et al.). IgE is added to a final concentration of 10 μg per ml of the Dulbecco's phosphate buffered saline. This solution is then divided into 500 μl aliquots. Serial dilutions of the purified catalytic antibodies are prepared and added to the IgE-containing aliquots. The reactions are placed at 37° C. and 100 μl samples removed at 0, 10, 30, 60, and 120 minutes. The aliquots are then loaded on an SDS-polyacrylamide gel and electrophoretically separated by SDS-PAGE. The proteins are then transferred to nitrocellulose filters (Ausubel et al.) and probed with a rabbit anti-human-IgE antibody conjugated to alkaline phosphatase.

Specific cleavage of the human IgE molecules by a catalytic antibody in target region I will generate three fragments of the IgE molecule under non-reducing conditions, two 50 kilodalton and a 150 kilodalton fragment.

Alternatively, specificity can be tested by cleavage of a labelled target peptide itself and analysis of the cleavage products as described above.

After a cleavage site is identified a number of variations of the target peptide sequence, with amino acid substitutions throughout the target region, can be generated by recombinant manipulation of the target peptide sequence. In this manner the sequence required for cleavage can be more specifically determined.

Although the invention has been described with respect to specific methods of making and using catalytic antibodies capable of cleaving specific IgE heavy chain sequences, it will be apparent that various changes and modifications may be made without departing from the invention. In particular, it will be recognized that the methods for clonal selection of $F_{ab}$ fragments capable of cleaving an IgE peptide may be applied to a variety of different peptides or proteins.

It is claimed:

1. A method of selecting genes encoding catalytic antibodies which are capable of cleaving a selected target peptide, comprising introducing into bacterial cells (i) a library of rearranged immunoglobulin genes in a cloning vector capable of expressing immunoglobulin genes in the cloning vector, under suitable expression conditions, and (ii) a phage vector bearing a phage gene encoding a gene product necessary for the production of infectious phage, where said gene is modified by introducing the target peptide coding sequence into the gene such that the resulting gene product inhibits production of infectious phage, and where cleavage of said target peptide results in an active gene product that allows production of infectious phage, growing the bacterial cells under conditions in which the immunoglobulin genes are expressed in the bacterial cells, screening the bacterial cells for production of infectious phage, and isolating the immunoglobulin genes associated with the infectious phage.

2. The method of claim 1, wherein said screening includes detecting the presence of infectious phage by plaque formation.

3. The method of claim 1, where said phage gene encodes a phage coat protein.

4. The method of claim 3, where said bacterial cells are *Escherichia coli* cells, said phage gene is introduced into gene III in such a fashion as to inhibit export of the gene III product to the periplasmic space of the bacterial cells.

5. The method of claim 1, wherein (i) said phage gene encodes a fused protein composed of a phage protein required for plaque formation, under selected growth conditions, to one end of the protein, and said target linking the second protein to the phage protein, and (ii) said screening includes detecting phage capable of producing plaques when grown under said selected growth conditions.

6. The method of claim 5, wherein said bacterial cells are *Escherichia coli* cells, said phage is a lambda phage, said phage protein is the cro protein, and the phage contains a temperature-conditional mutation in its genomic cro gene which is inactive above a selected temperature, and said screening is performed above said selected temperature.

7. The method of claim 6, wherein said phage protein is the lambda cro protein, and said second protein is the *Escherichia coli* colicin E1 immunity protein.

8. A method of producing a catalytic antibody effective to cleave a target peptide sequence, comprising introducing into bacterial cells (i) a library of rearranged immunoglobulin genes in a cloning vector capable of expressing immunoglobulin genes in the cloning vector, under suitable expression conditions, and (ii) a phage vector bearing a phage gene encoding a gene product necessary for the production of infectious phage, where said gene is modified by introducing the target peptide coding sequence into the gene such that the resulting gene product inhibits production of infectious phage, and where cleavage of said target peptide results in an active gene product that allows production of infectious phage, growing the bacterial cells under conditions in which the immunoglobulin genes are expressed in the bacterial cells, screening the bacterial cells for production of infectious phage, isolating the immunoglobulin genes associated with the infectious phage, and expressing the isolated immunoglobulin genes in a suitable expression system.

* * * * *